United States Patent
Lewis

(10) Patent No.: US 10,772,825 B2
(45) Date of Patent: Sep. 15, 2020

(54) MARINE EXTRACT COMPOSITIONS AND METHODS OF USE

(71) Applicant: Marine Biology & Environmental Technologies, LLC, Tarzana, CA (US)

(72) Inventor: Eric Lewis, Tarzana, CA (US)

(73) Assignee: Marine Biology % Environmental Technologies, LLC, Tarzana, CA (US)

( * ) Notice: Subject to any disclaimer, the term of this patent is extended or adjusted under 35 U.S.C. 154(b) by 0 days.

(21) Appl. No.: 15/099,473

(22) Filed: Apr. 14, 2016

(65) Prior Publication Data

US 2016/0228352 A1    Aug. 11, 2016

Related U.S. Application Data

(63) Continuation of application No. 14/054,458, filed on Oct. 15, 2013, now abandoned.

(60) Provisional application No. 61/714,199, filed on Oct. 15, 2012, provisional application No. 61/714,200, filed on Oct. 15, 2012, provisional application No. 61/714,201, filed on Oct. 15, 2012, provisional application No. 61/714,203, filed on Oct. 15, 2012, provisional application No. 61/714,204, filed on Oct. 15, 2012.

(51) Int. Cl.

| *A61K 35/618* | (2015.01) |
|---|---|
| *A61K 8/98* | (2006.01) |
| *A61K 45/06* | (2006.01) |
| *A61Q 19/00* | (2006.01) |
| *A61Q 19/08* | (2006.01) |
| *A61Q 17/04* | (2006.01) |
| *A61Q 19/02* | (2006.01) |

(52) U.S. Cl.
CPC ............ *A61K 8/987* (2013.01); *A61K 35/618* (2013.01); *A61K 45/06* (2013.01); *A61Q 17/04* (2013.01); *A61Q 19/00* (2013.01); *A61Q 19/005* (2013.01); *A61Q 19/007* (2013.01); *A61Q 19/02* (2013.01); *A61Q 19/08* (2013.01); *A61K 2800/522* (2013.01); *A61K 2800/596* (2013.01); *A61K 2800/70* (2013.01)

(58) Field of Classification Search
CPC ....... A61K 36/00; A61K 36/02; A61K 35/618
USPC .............................. 424/725, 538, 548, 78.08
See application file for complete search history.

(56) References Cited

U.S. PATENT DOCUMENTS

| 2004/0018166 A1 | 1/2004 | Chen et al. | |
| 2004/0043961 A1* | 3/2004 | Wu .......................... | A61K 8/73 514/54 |

FOREIGN PATENT DOCUMENTS

| JP | 2006089385 A * | 4/2006 | |
| WO | WO 2010143879 A2 * | 12/2010 | ............. A61K 8/987 |

OTHER PUBLICATIONS

Fabiola Lafarga de la Cruz1,2 and Cristian Gallardo-Esca rate "Intraspecies and interspecies hybrids in Haliotis: natural and experimental evidence and its impact on abalone aquaculture", Reviews on aquaculture (2011) 3, pp. 74-99.*
Comparison of n-3 polyunsaturated fatty acid contents of wild and cultured, Australian abalone vol. 55, 2004—Issue 2 Journal International Journal of Food Sciences and Nutrition.*
Notman et al."Molecular Basis for Dimethylsulfoxide (DMSO) Action on Lipid Membranes", Journal of American Chemical Society, 2006, 128, 13982-13983.*
Ines Sjerobabski-Masnec and Mirna Šitum, "Skin Aging", Acta Clin Croat 2010; 49:515-519. published 2010.
Il Liu, H Ma, and Y Li, "Interventions for the treatment of stretch marks: a systematic review". Cutis. 94 (2): 66-72. (Aug. 2014).

* cited by examiner

*Primary Examiner* — Terry A McKelvey
*Assistant Examiner* — Deborah A Davis
(74) *Attorney, Agent, or Firm* — The Fedde Law Firm; Kenton Fedde; Nathaniel Fedde

(57) ABSTRACT

Compositions comprising extracts from marine organisms show beneficial effects on skin ailments. Fine lines, wrinkles, and sagging in skin are improved with the application of compositions with marine extracts. Production of collagen, elastin and hyaluronic acid are increased after application of the compositions.

12 Claims, 6 Drawing Sheets

MARINE EXTRACT COMPOSITIONS AND METHODS OF USE

CROSS-REFERENCE TO RELATED APPLICATIONS

This application is a continuation of U.S. application Ser. No. 14/054,458, which claims priority to U.S. Provisional Application Nos. 61/714,199, 61/714,200, 61/714,201, 61/714,203 and 61/714,204, which were filed on Oct. 15, 2012; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

Skin is affected by many factors, including ultraviolet light, air & topical pollution, wind, heat, humidity, soaps, and other environmental elements. Additionally, biological changes, including chronological age, health and life style can effect the quality of the skin.

Typical skin problems are fine lines, wrinkles, and sagging. Aging and sun damage to the skin causes alteration, destruction and diminished biosynthesis of the major components of the dermis (the second layer of the skin). When we consider aging skin we are generally thinking about the visible effects: sagging, wrinkled skin with a coarse texture, large pores and increasing numbers of lentigines (small pigmented spots) and actinic keratoses (a growth of precancers on the skin). The principal cause of skin aging is two-fold; a slowdown in the production of extra cellular matrix (ECM) component which is accompanied by a diminished capacity to handle the production workload efficiently. The causes of visible aging skin are related to diminished biosynthesis of the three major components of the ECM: collagen, elastin and hyaluronic acid. Where we observe sun damage and aging of the skin, we observe the loss of these building blocks of our skin. In addition, fibrocytes, the cells which make collagen, elastin and hyaluronic acid and microcirculation, which nourish the skin also decreases in number and function by about 3% per year after the age of 30.

Collagen gives strength and toughness to the skin. It acts as scaffolding for elastin and hyaluronic acid. Loss of collagen results in weak and easily torn skin.

Elastin gives the elastic rebound. Skin loses its bounce with the loss of elastin. This results in skin having a crêpey appearance with a wrinkled surface and thin skin with a tendency to sag.

Hyaluronic acid gives the skin volume and provides a great deal of protective insulation. Loss of hyaluronic acid leads to thin, translucent skin, where blood vessels appear more prominent and the microvasculature becomes visible. The skin appears pink and displays the epidermal aspects of sun damage, which include "liver" (age) spots, which in reality are sunspots (called lentigines). The skin also becomes easily bruised and torn.

These are the supporting structures of the skin; collagen fibers provide the scaffolding that supports the epidermis, while elastin fibers give the skin its resiliency and firmness. Hyaluronic acid is made up of long chain sugar molecules that form a gel that holds up to 6,000 times its weight in water. Hyaluronic acid is essential to healthy skin because it increases the water content of the epidermis and gives the skin its pleasing plumpness and pliability.

People start losing these essential components of skin at a young age and sun damage contributes dramatically more loss. After age 30, the amounts of collagen, elastin and hyaluronic acid decreases about 1-2% per year, and aging and sun damage combined can cause a loss of these essential components upwards of 3% per year.

In addition the ratio of healthy new cells to defective cells (that look like unsightly age spots, etc.) shrinks. Replacement of new tissue takes longer (cell turnover rate slows), so in addition to wrinkles and sagging the skin becomes dull, coarse, blotchy and hyperpigmented.

The reason behind this litany of negative effects is simple and familiar; as a person ages, hormone production slows down. Hormone insufficiency dictates a slowdown of a number of processes, including those affecting the appearance of the skin.

Aging and sun damage also dramatically reduce the number and activity of oil glands (called sebaceous glands) in the dermis. These glands also secrete the body's natural sunscreen (called squalene). The epidermis (the outer layer of the skin) then becomes dry and cracked and less protective.

The deterioration of the dermis directly affects the epidermis. Epidermal cell division decreases, the replacement of old tissue with new, healthy cells takes longer. The skin becomes thin and vulnerable. In this condition, the skin is more sensitive to outside contactants. Contactants are allergens that can cause dermatitis.

Injections of collagen or hyaluronic acid add no more than temporary improvement. They do not organize those materials in a functional pattern. The materials are placed in globs that fill in the deterioration of the skin's natural composition. The effect of injections doesn't last because the collagen, elastin and hyaluronic acid are torn down by the fibroclasts. There is no improvement in the number or function of fibrocytes and blood vessels.

There are many products available over the counter or from a physician that are directed toward improving the health and physical appearance of the skin. The products try to delay or minimize the production of wrinkles or even try to eliminate wrinkles once they have formed.

Consumers prefer topically applied products due to their ease of use. The strongest topical treatment on the market is currently Retin-A cream. Others include alpha hydroxy acid and vitamin C creams. These have been shown to minimally increase collagen production. They do nothing to increase elastin and hyaluronic acid, or number and function of fibrocytes or blood vessels. Although the skin may appear better after treatment, there is still the same number of cells after treatment as there were before treatment. Once treatment is stopped, the skin returns to the pre-treatment status in about 1 to 2 weeks. This may be due to the cells overworking during the Retin-A treatment, which may shorten the cells life span.

Scientists around the world are increasingly recognizing the rejuvenating powers of the ocean. They realize that the same forces that created life play a huge role in regenerating life. People are interested in using natural or organic products for skin care in the belief that these products are safer and more effective. Of interest to these people are products from the ocean. Organisms from the ocean are believed to have beneficial compounds and salts.

A focus has been placed on marine algae and organisms that eat algae since they will concentrate the compounds form the algae. The abalone (*Haliotis* spp.), in particular, has been investigated for its beneficial effects. There have been reports that abalone has antiviral and antibacterial activity when injected into mice. Also, there is antidotal evidence that the guts from abalone contain a photoactive chemical that causes cats to have skin damage after exposure to light. Additionally, the severity of the skin damage varies during the year.

While there are many products that take advantage of the flora from the sea by adding macroalgae extracts there are very few that are using marine fauna. Adding biopeptides from gastropods is a cutting-edge idea. This idea, which is about to transform anti-aging skin care as we know it, is complemented by the unique extraction technology that compromises neither product efficacy nor customer safety.

The desire of the public for products from the ocean and suggestions that some marine organisms contain unknown chemicals led to the investigation of extracts from several marine organisms—algae, cyanobacteria and animals.

SUMMARY OF THE INVENTION

The investigation of extracts from marine organisms led to findings of extracts that stimulate the production of cellular products and hormones involved in regulating crucial skin regenerative processes.

Extracts from algae and seaweed contain peptides which speed healing by promoting cell growth, nourishing the skin with vitamins and minerals and enhancing barrier function. Adding the peptides places the stimulant and the raw materials in the same application. Instead of adding the raw materials alone, including the stimulants to organize these raw materials recreates the natural function of the skin.

Probably the most dramatic impact of aging and sun damage is the death of fibrocytes, which create and maintain skin and its components and the proliferation of fibroclasts which dissolve degenerating components. The net result is that the skin decreases 2-3% of its collagen, elastin and hyaluronic acid, fibrocytes and blood vessels each year after the age of 30. There is no substance, no cream that has ever been shown to increase fibrocyte and blood vessel formation in the skin. The extract incorporates the natural building blocks into functional skin by stimulating not only the reproduction of fibrocytes but also new collagen, elastin and hyaluronic acid in patterns that maximize skin function.

The effect of creams and injectables containing collagen, elastin and hyaluronic acid is temporary at best and far less functional. Simply providing the raw materials does not incorporate them into the skin. Only the fibrocytes and fibroblasts will do this.

Among the components in the extracts are specific concentrations of three prostaglandin subtypes that improve the scaffolding of the dermis by stimulating the fibrocytes to produce more collagen, elastin and hyaluronic acid.

Fibrocytes do far more than produce collagen, elastin and hyaluronic acid. They organize these substances into a highly functional unit called the dermis, which is the "cow hide" or "body" of the skin.

Fibroclasts are cells that dissolve damaged and altered collagen, elastin and hyaluronic acid. This is an essential function. Unless the fibroclasts dissolve damaged skin and the fibrocytes replace what the fibroclasts have taken away with new, intact skin, age and sun damage will impair skin function and rob the skin of its healthy look.

With age, however, and as sun damage occurs, fibroclastic activity dominates over fibrocytic activity. Without fibrocytes to replace what the fibroclasts take away, the skin loses functionality. We see degeneration and are left with thinner, weaker, less functional skin. The decreased fibrocytic activity and increased fibroclastic activity deteriorate the skin and also reduce its ability to regenerate itself.

An action of the extracts is that the stimulation of the fibrocytes to reproduce. Compared to the diminished ability of aged and sun damaged skin, the extracts provide an exponential increase in collagen, elastin and hyaluronic acid. The sheer level of production of these substances is unmatched by any competing product. It can only be explained by the direct stimulation of fibrocytes to divide into fibroblasts (juvenile fibrocytes). It is the only way to recreate the youth of the skin. The extracts create young, plump, highly productive fibroblasts.

The extracts are more effective than any "rejuvenating" cream on the market today because they stimulate the fibrocytes to do more than produce collagen, elastin and hyaluronic acid: it stimulates the fibrocytes to divide into fibroblasts. Thereby, the extracts rejuvenate the skin in a much quicker, more functional and long lasting way. Without this action, the improvement would be slow, linear and temporary. By stimulating the production of fibrocytes, the improvement becomes more exponential and permanent. The difference in action is obvious to the eye.

Other products achieve only a minor stimulation of existing fibrocytes. They could never improve the overall skin quality the way these extracts are able to do it. The extracts have shown to be effective in even the most aged and sun damaged skin. The extracts actions go beyond the normal capability of aging skin. They act as a "reset button" both visually and microscopically.

As the extracts stimulate the dermis to become healthier, the dermis in turn stimulates cell reproduction in the epidermis. This creates healthier skin altogether: smoother, fuller, and less blotchy. The extracts improve the entire skin which is different than other products. While this improvement originates below the surface in the dermis, the extracts also improve the metabolism and reproduction of the epidermis directly.

Stimulation from a single topical application can last up to three to four weeks and the effects seem to be permanent. After maximizing the stimulation by front-loading the product, maintenance applications will continue to provide improvement by raising the levels of the three major, structural components of the skin and increasing the number of fibrocytes that produce these building blocks and blood vessels which nourish them.

The extracts work with nature to give back to the skin what the aging process has taken away from it, components that are destroyed, diminished or altered in both the aging and the sun-damaged skin.

These same stimulating actions of not only increasing fibroblast and blood vessel numbers and function but also collagen, elastin and hyaluronic acid production have been shown to improve the speed and quality of healing wounds, especially in older people. Several patients have used the extracts on dressings with tremendous success on recalcitrant ulcers of bed sores and diabetics. These extracts are also expected to dramatically improve the healing of third degree burns. Formal FDA studies are planned.

The active components in the extracts fight pre-cancers and the structure of the dermis and epidermis that creates them. Research indicates that the extracts are delivered through the Langerhans cells. Langerhans cells have "fingers" that reach into the epidermis to deliver the active chemicals in the extracts and further stimulate the T cell mediated immune system.

The extracts decrease sunspots (lentigines) and vascular blemishes, not to mention the substantial improvement of the overall quality and thickness of the skin. The extracts improves the thickness of the skin in patients with Rosacea, which camouflages the underlying blood vessels. A thicker dermis does not influence the flushing episodes; it changes the appearance of the blood vessels. The skin is thicker and thereby covers the blood vessels.

Additionally, the extracts improve the overall health of the epidermis and dermis to improve the skin barrier in patients with dry, irritated and sensitive skin. This results in less irritation and better resistance to infection. It also allows for further hydration of a much thicker dermis and epidermis.

The improved barrier function and faster cell turnover rate means the skin is better able to prevent further damage in sun damaged skin while repairing existing damage. By improving the skin's health, the extracts also improve secretion by the sebaceous glands, which produce natural oils including squalene, the body's natural sunscreen. This further protects the increasingly healthy, treated skin.

Natural marine extracts stimulate the immune system to kill pre-cancers, and to produce more blood vessels and fibrocytes. Plus stimulating the fibrocytes themselves to produce more collagen, elastin and hyaluronic acid.

It will be clearly understood that while the invention is described in detail with reference to compounds detected in the viscera, these compounds, when present in or extracted from whole animals or parts thereof, are still within the scope of the invention. The disclosure includes compositions comprising an active compound as described above, together with a pharmaceutically-suitable carrier or diluent.

Methods are disclosed for treating or alleviating damage to skin, caused by ultraviolet irradiation, ionizing radiation, microwave radiation, exposure to ozone, or the like, comprising the step of topically administering an effective amount of a disclosed compound to a subject in need of such treatment. It may be used in the treatment of solar keratosis and skin damage occurring during radiotherapy.

The mammal may be a human, or may be a domestic or companion animal. While it is particularly contemplated that the compounds of the invention are suitable for use in medical and cosmetic treatment of humans, it is also applicable to veterinary treatment, including treatment of companion animals such as dogs and cats, and domestic animals such as horses, cattle and sheep, or zoo animals such as felids, canids, bovids, and ungulates.

The disclosed compounds and compositions may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case. It is contemplated that compounds of the invention may be administered topically. Methods and pharmaceutical carriers for preparation of pharmaceutical compositions are well known in the art.

For the purposes of this specification it will be clearly understood that the word "comprising means including but not limited to" and that the word "comprises" has a corresponding meaning.

DETAILED DESCRIPTION OF THE INVENTION

Figure 1:
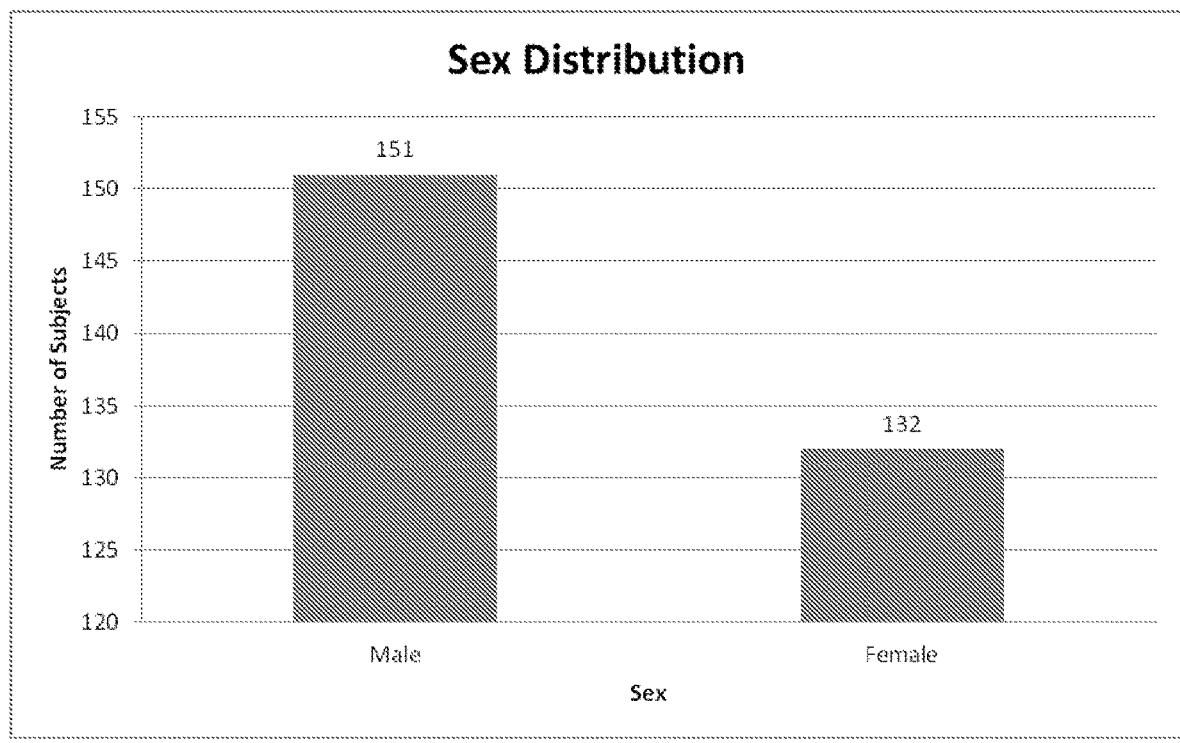
FIG. 1 shows the sex distribution of the patients in the study of the extract composition.

The extracts work to reverse the skin aging process and improve and unsightly damaged skin and pre-cancers. The extracts cause the stimulation of the following productive processes, increase collagen production, increase elastin production, increase hyaluronic acid production and improve cell turnover rate The results from application of the extracts, as determined by in vivo trials, showed that the dermis becomes thicker giving smoother surface appearance, skin becomes firmer with less sagging, diminished number of disfiguring age spots while the old ones fade and new ones do not appear, skin has a more consistently even appearance as healthy epidermal layers replace damaged areas, skin texture improves as healthy cells outnumber defective cells and sufficient supplies of HA ensure that skin appears hydrated, less wrinkled and healthy Abalone Extract The extract stimulates the T-cell mediated immune system through the Langerhans cells. The stimulation can last up to three to four weeks. The results were quantified with the use of a Canfield Visia Computerized Imaging System.

In addition, abalone extract stimulates fibrocysts (fibroblasts) to produce collagen, elastin and hyaluronic acid in the dermis of the skin. Other rejuvenating creams on the market today either directly provide collagen, hyaluronic acid and elastin which the skin can not efficiently utilize or they provide peptides which cannot stimulate the biosynthesis of collagen, hyaluronic acid and elastin as effectively as the extract. The extract does the best job of working with nature to give back what the aging process has taken away. These are the components of the skin which are destroyed, diminished or altered in both the aging and the sun-damaged skin. The collagen provides strength and toughness to the skin; its loss creates very feeble, easily torn skin. The elastin provides elastic rebound and without it, the skin has tremendous wrinkling and "hangs". The hyaluronic acid provides the "substance" or thickness of the skin. Without it, the skin becomes thin (at times translucent) and bruises very easily. Abalone extracts works better than all of the "rejuvenating" creams on the market today.

The beneficial effects of abalone extracts were thoroughly tested and quantified by using a "wrinkle index" and precise skin thickness measurements on the Canfield Imaging System.

These same stimulating actions of not only increasing fibroblast and blood vessel numbers and function but also collagen, elastin and hyaluronic acid production have been shown to improve the speed and quality of healing wounds, especially in older people. Several patients have used the extracts on dressings with tremendous success on recalcitrant ulcers of bed sores and diabetics. These extracts are also expected to dramatically improve the healing of third degree burns. Formal FDA studies are planned.

Body Structure of Abalone

Abalone have a simple body structure with a large columnar muscle attached to the muscular foot, and a visceral mass, attached to the left side of the columnar muscle, which wraps around the columnar muscle to the right. The visceral mass includes the gills, stomach, heart and conical appendage. The conical appendage includes the digestive gland, which is surrounded by the gonad. The sexes are separate in abalone with individuals either male (testes) or female (ovary).

Body Structure of Bivalves

The visceral mass is located between a pair of shells. The pair of adductor muscles open and close the shells to allow respiratory and feeding. The sexes can be separate with male and female individuals or they can be hermaphroditic with both sexes present.

Body Structure of Sea Cucumber

Sea Cucumbers are soft-bodied echinoderms typically vermiform in shape. It is radially symmetrical along its longitudinal axis. Inside the body wall is the coelom which is divided by three longitudinal mesenteries which surround and support the internal organs.

Body Structure of Crustacean

Crustaceans have a hard exoskeleton protecting the visceral mass. The visceral mass can be generally separated into 3 tissues—muscle, viscera and gonad.

Tissue Preparation—Abalone
 a. The animal is removed from its shell.
 b. The visceral mass is separated from the columnar muscle.
 c. The conical appendage is cut-off from the visceral mass to obtain two tissue samples.
 d. The conical appendage includes the digestive gland and gonad tissue
 d. The gonad surrounding the digestive is removed and kept as a separate tissue sample.
 e. The abalone is divided into 5 separate tissue samples—columnar muscle/foot, viscera, digestive gland, testes and ovary.

Tissue Preparation—Bivalve
 a. The animal is removed from its shell.
 b. The visceral mass is separated from the adductor muscles.
 c. The visceral mass can be further prepared by removing the gonad
 e. The bivalve is divided into 3 separate tissue samples—adductor muscle, viscera, and gonad.

Tissue Preparation—Sea Cucumber
 a. The body of the animal is sliced along the length of the body to expose the viscera.
 b. The gonad is separated visceral mass.
 c. The 5 muscles are removed from the body wall.
 e. The sea cucumber is divided into 4 separate tissue samples—body wall, muscle, viscera, and gonad.

Tissue Preparation—Crustacean
 a. The outer exoskeleton is removed and the visceral mass is collected.
 b. the gonad and muscles are removed from the visceral mass.
 e. The crustacean is divided into 4 separate tissue samples—exoskeleton, muscle, viscera, and gonad.

Tissue Preparation—Algae/Cyanobacteria
 a. New, actively growing fronds are removed from macroalgae.
 b. The whole organism is collected and concentrated for microalgae and cyanobacteria Extraction Process The tissue sample is obtained from the organism and stored on ice until a sufficient quantity of tissue is obtained.

The tissue can either be frozen for processing at a future time or transferred directly to the next step in the process. If the tissue is frozen, it can be further processed by freeze drying/lyophilization to increase shelf life.

The collected tissue is placed in a blender, homogenizer, grinder or similar machine to mechanically break up the cells in the tissue.

Optionally, the tissue can be directly extracted with an appropriate polar and/or non-polar solvent (water, alcohol, hexane, chloroform, ether, or other suitable solvent) to obtain fractions containing active compounds or the tissue can be passed to the next step with extraction with a solvent.

If the tissue was not freeze dried after the collection step and processed as fresh tissue, the processed tissue is frozen/freeze dried or just dried.

The dried tissue is place into a mortar and pounded with a pestle to make a powder. The collagen can be separated from the powder by screen filtering. The collagen gets caught in the screen, and the powder falls through. The collagen is discarded.

If the tissue sample has not already been extracted with solvents, the powder is extracted with polar and/or non-polar solvents to obtain fractions with the active compounds.

The tissue sample can be centrifuged or filtered to remove cellular debris. Also, the solvent fraction can be further processed by column chromatography, HPLC or other similar separation technique.

The powder is reconstituted in an appropriate carrier solvent or the fractions obtained by extracting the powder are mixed with a delivery vehicle.

The reconstituted powder is used in the disclosed compositions.

Observed Results of Extracts from Abalone, Bivalves, Sea Cucumbers, Crustaceans, Algae and Cyanobacteria The extracts rejuvenated the skin with increased production of fibrocytes and new blood vessels. Elastin, collagen and hyaluronic acid production was stimulated to allow the skin to regain elastic rebound, thickness and strength. Stretch marks, wrinkles, laugh lines, fold lines and muscle-wrinkles disappeared after the application of the extracts.

The extracts resolved problems with thin, fragile, easily torn skin due to age and/or sun damage. Additionally, the extracts caused the disappearance of skin ulcers in elderly and diabetics patients, pre-cancerous lesions on the skin, translucence of the skin in the elderly, and rosacea. The treatments with the extracts caused a reduction or disappearance of hot flashes in the face, less bruising, improved healing of wounds.

The results were permanent (subject to the normal rate of aging) with a disappearance of pre-cancerous lesions, sunspots (lentigines) and vascular blemishes.

Definitions

Extract—the term "extract" as used in this disclosure refers to 1) a preparation containing the active ingredient of a substance in concentrated form; 2) a solution of plant or animal tissue containing an active principle; 3) a solid, viscid, or liquid substance containing the essence or active substance of a food, plant, or drug in concentrated form; 4) obtaining a substance by chemical or mechanical action, as by pressure, distillation, or evaporation; 5) obtaining a substance from a mixture or material by a chemical or physical process, such as distillation, the action of a solvent, or separation by a physical characteristic of a chemical or compound (e.g., molecular weight; size; shape; affinity, relative affinity or lack of affinity to a solvent or affinity, relative affinity or lack of affinity between a gel and a solvent; etc.). An extract is a complex mixture of chemicals and compounds, whose composition (quantity and ratio of compounds) is determined by various factors, including the tissue extracted, species of organism, solvent or solvents used during the extraction and order of steps in the extraction process. Two extracts will be different if the factors during the extraction process are different.

Fraction—A chemical component separated by fractionation. A quantity collected from a sample or batch of a substance during fractionation where a mixture is separated into different parts. The separable constituents of a substance, tissue or mixture.

Fractionation—a separation process in which a certain quantity of a mixture (solid, liquid or suspension) is divided up in a number of smaller quantities (fractions) in which the composition varies according to the selection criteria (e.g., molecular weight; size; shape; affinity, relative affinity or lack of affinity to a solvent or affinity, relative affinity or lack of affinity between a gel and a solvent; etc.). Fractions are collected based on differences in a specific property of the individual components. Fractionation of components also takes place in column chromatography by a difference in affinity between stationary phase and the mobile phase.

Tissue—the term "tissue" as used in this disclosure means the collective group of cells, tissues or organs associated together in an organism identified by a common name; e.g., frond, gonad, viscera, columnar muscle, digestive gland, conical appendage, etc. The term "tissue" as used in this disclosure is not limited to the scientific classification of the four basic types of tissue: muscle, nerve, epidermal, and connective.

Abalone tissue extract—an extract obtained from any tissue from an abalone.

Alga tissue extract—an extract obtained from any tissue from an alga.

Bivalve tissue extract—an extract obtained from any tissue from a bivalve.

Crustacean tissue extract—an extract obtained from any tissue from a crustacean.

Cyanobacteria extract—an extract obtained from a cyanobacteria.

Molluscan tissue extract—an extract obtained from any tissue from a mollusc.

Sea cucumber tissue extract—an extract obtained from any tissue from a sea cucumber.

Marine—the term "marine" as used in this disclosure refers to organisms (animals, plant and cyanobacteria) that live in water with at least some salinity. The water could be called oceanic, sea, brackish or estuarine. Marine is to be given its widest meaning for water with salt.

Drying—any method that reduces the water content, including natural air drying, supercritical drying, freeze drying, lyophilization, convective or direct drying, spray drying, drum drying, vacuum drying, microwave, refractance window drying, infrared zone drying and simple dehydration.

Other Ingredients

The disclosed compositions can comprise one or more of the following cosmetic product as an ingredients acetyl hexapeptide-3 (argirilene), acrylates/$C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis*, *Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis*, *Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, saccharomyces ferment, *Salvia hispanica* (chia) seed oil, *Sclerocarya birrea* (manila) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Species of Abalone—*Haliotis*

*Haliotis albicans, Haliotis aleata, Haliotis alfredensis, Haliotis alternata, Haliotis ancile, Haliotis aquatilis, Hali-* otis asinina, Haliotis asinum, Haliotis assimilis, Haliotis astricta, Haliotis aulaea, Haliotis aurantium, Haliotis australis, Haliotis barbouri, Haliotis bonita, Haliotis brazieri, Haliotis brazieri hargravesi, Haliotis caelata, Haliotis californiana, Haliotis californiensis, Haliotis canaliculata, Haliotis canariensis, Haliotis capensis, Haliotis carinata, Haliotis cingulata, Haliotis clathrata, Haliotis coccinea, Haliotis coccoradiata, Haliotis concinna, Haliotis conicopora, Haliotis corrugata, Haliotis corrugata corrugata, Haliotis corrugata oweni, Haliotis costata, Haliotis cracherodii, Haliotis cracherodii californiensis, Haliotis cracherodii cracherodii, Haliotis crebrisculpta, Haliotis crenata, Haliotis cruenta, Haliotis cunninghami, Haliotis cyclobates, Haliotis dalli, Haliotis dalli dalli, Haliotis dalli roberti, Haliotis dentata, Haliotis desussata, Haliotis diegoensis, Haliotis discus, Haliotis discus discus, Haliotis discus hannai, Haliotis dissona, Haliotis diversicolor, Haliotis diversicolor diversicolor, Haliotis diversicolor squamata, Haliotis diversicolor supertexta, Haliotis dohrniana, Haliotis dringii, Haliotis drogini, Haliotis echinata, Haliotis elatior, Haliotis elegans, Haliotis elevata, Haliotis ethologus, Haliotis excavata, Haliotis exigua, Haliotis expansa, Haliotis fatui, Haliotis ficiformis, Haliotis fulgens, Haliotis fulgens fulgens, Haliotis fulgens guadalupensis, Haliotis fulgens turveri, Haliotis fulgens walallensis, Haliotis funebris, Haliotis gemma, Haliotis gibba, Haliotis gigantea, Haliotis gigas, Haliotis glabra, Haliotis granti, Haliotis granulata, Haliotis grayana, Haliotis gruneri, Haliotis guadalupensis, Haliotis guineensis, Haliotis hanleyi, Haliotis hargravesi, Haliotis hattorii, Haliotis holzneri, Haliotis howensis, Haliotis imperforata, Haliotis improbula, Haliotis incisa, Haliotis iris, Haliotis jacnensis, Haliotis jacnensis jacnensis, Haliotis janus, Haliotis japonica, Haliotis jousseaumi, Haliotis kamtschatkana, Haliotis kamtschatkana assimilis, Haliotis kamtschatkana kamtschatkana, Haliotis kraussi, Haliotis laevigata, Haliotis lamellosa, Haliotis latilabris, Haliotis lauta, Haliotis lucida, Haliotis lusus, Haliotis madaka, Haliotis marfaloni, Haliotis mariae, Haliotis marmorata, Haliotis melculus, Haliotis midae, Haliotis multiperforata, Haliotis mykonosensis, Haliotis naevosa, Haliotis nebulata, Haliotis neglecta, Haliotis nodosa, Haliotis ovina, Haliotis ovina ovina, Haliotis ovina volcanius, Haliotis oweni, Haliotis papulata, Haliotis parva, Haliotis patamakanthini, Haliotis pellucida, Haliotis pertusa, Haliotis picta, Haliotis planata, Haliotis planilirata, Haliotis ponderosa, Haliotis pourtalesii, Haliotis pourtalesii aurantium, Haliotis pourtalesii pourtalesii, Haliotis pulcherrima, Haliotis pustulata, Haliotis pustulifera, Haliotis queketti, Haliotis reticulata, Haliotis revelata, Haliotis roberti, Haliotis roedingi, Haliotis roei, Haliotis rosacea, Haliotis rosea, Haliotis ruber, Haliotis rubicunda, Haliotis rubiginosa, Haliotis rubra, Haliotis rubra conicopora, Haliotis rubra rubra, Haliotis rufescens, Haliotis rugosa, Haliotis rugosoplicata, Haliotis sanguinea, Haliotis scabricostata, Haliotis scalaris, Haliotis scalaris scalaris, Haliotis scutulum, Haliotis semiplicata, Haliotis semistriata, Haliotis sieboldii, Haliotis sinuata, Haliotis smithsoni, Haliotis sorenseni, Haliotis spadicea, Haliotis splendens, Haliotis splendidula, Haliotis squamata, Haliotis squamosa, Haliotis stomatiaeformis, Haliotis striata, Haliotis strigata, Haliotis subvirginea, Haliotis sulcosa, Haliotis supertexta, Haliotis tayloriana, Haliotis thailandis, Haliotis tomricei, Haliotis tricostalis, Haliotis tricostata, Haliotis tuberculata, Haliotis tuberculata coccinea, Haliotis tuberculata tuberculata, Haliotis tubifera, Haliotis turveri, Haliotis tuvuthaensis, Haliotis unilateralis, Haliotis varia, Haliotis varia dohrniana, Haliotis varia planata, Haliotis venusta, Haliotis virginea, Haliotis virginea virginea, Haliotis viridis, Haliotis vixlirata, Haliotis volcanius, Haliotis vulgaris, Haliotis walallensis, Haliotis whitehousei, Haliotis zealandica, and Haliotis ziczac.

Embodiments

In one embodiment of the disclosed extraction method the tissue is the visceral mass. In one embodiment of the disclosed extraction method the tissue is the conical appendage. In one embodiment of the disclosed extraction method the tissue is the digestive gland. In one embodiment of the disclosed extraction method the tissue is the testes. In one embodiment of the disclosed extraction method the tissue is the ovary. In one embodiment of the disclosed extraction method the tissue is the whole organism.

Abalone

In one embodiment of the disclosed composition, the composition comprises from 1% to 100% of a whole body extract, visceral extract, conical appendage extract, digestive gland extract, testes extract, ovary extract or combination of extracts of *Haliotis* spp. In one embodiment of the disclosed composition, the composition comprises from 10% to 100% of a whole body extract, visceral extract, conical appendage extract, digestive gland extract, testes extract, ovary extract or combination of extracts of *Haliotis* spp. In one embodiment of the disclosed composition, the composition comprises from 20% to 100% of a whole body extract, visceral extract, conical appendage extract, digestive gland extract, testes extract, ovary extract or combination of extracts of *Haliotis* spp. In one embodiment of the disclosed composition, the composition comprises from 35% to 100% of a whole body extract, visceral extract, conical appendage extract, digestive gland extract, testes extract, ovary extract or combination of extracts of *Haliotis* spp. In one embodiment of the disclosed composition, the composition comprises from 35% to 80% of a whole body extract, visceral extract, conical appendage extract, digestive gland extract, testes extract, ovary extract or combination of extracts of *Haliotis* spp. In one embodiment of the disclosed composition, the composition comprises from 35% to 60% of a whole body extract, visceral extract, conical appendage extract, digestive gland extract, testes extract, ovary extract or combination of extracts of *Haliotis* spp. In one embodiment of the disclosed composition, the composition comprises from 20% to 50% of a whole body extract, visceral extract, conical appendage extract, digestive gland extract, testes extract, ovary extract or combination of extracts of *Haliotis* spp.

In one embodiment of the disclosed composition, the composition comprises from 1% to 100% of a whole body extract, visceral extract, conical appendage extract, digestive gland extract, testes extract, ovary extract or combination of extracts of *Haliotis fulgens*. In one embodiment of the disclosed composition, the composition comprises from 10% to 100% of a whole body extract, visceral extract, conical appendage extract, digestive gland extract, testes extract, ovary extract or combination of extracts of *Haliotis fulgens*. In one embodiment of the disclosed composition, the composition comprises from 20% to 100% of a whole body extract, visceral extract, conical appendage extract, digestive gland extract, testes extract, ovary extract or combination of extracts of *Haliotis fulgens*. In one embodiment of the disclosed composition, the composition comprises from 35% to 100% of a whole body extract, visceral extract, conical appendage extract, digestive gland extract, testes extract, ovary extract or combination of extracts of *Haliotis fulgens*. In one embodiment of the disclosed composition, the composition comprises from 35% to 80% of a whole body extract, visceral extract, conical appendage extract, digestive gland extract, testes extract, ovary extract or combination of extracts of *Haliotis fulgens*. In one embodiment of the disclosed composition, the composition comprises from 35% to 60% of a whole body extract, visceral extract, conical appendage extract, digestive gland extract, testes extract, ovary extract or combination of extracts of *Haliotis fulgens*. In one embodiment of the disclosed composition, the composition comprises from 20% to 50% of a whole body extract, visceral extract, conical appendage extract, digestive gland extract, testes extract, ovary extract or combination of extracts of *Haliotis fulgens*.

In one embodiment of the disclosed composition, the composition comprises from 1% to 100% of a whole body extract, visceral extract, conical appendage extract, digestive gland extract, testes extract, ovary extract or combination of extracts of *Haliotis rufescens*. In one embodiment of the disclosed composition, the composition comprises from 10% to 100% of a whole body extract, visceral extract, conical appendage extract, digestive gland extract, testes extract, ovary extract or combination of extracts of *Haliotis rufescens*. In one embodiment of the disclosed composition, the composition comprises from 20% to 100% of a whole body extract, visceral extract, conical appendage extract, digestive gland extract, testes extract, ovary extract or combination of extracts of *Haliotis rufescens*. In one embodiment of the disclosed composition, the composition comprises from 35% to 100% of a whole body extract, visceral extract, conical appendage extract, digestive gland extract, testes extract, ovary extract or combination of extracts of *Haliotis rufescens*. In one embodiment of the disclosed composition, the composition comprises from 35% to 80% of a whole body extract, visceral extract, conical appendage extract, digestive gland extract, testes extract, ovary extract or combination of extracts of *Haliotis rufescens*. In one embodiment of the disclosed composition, the composition comprises from 35% to 60% of a whole body extract, visceral extract, conical appendage extract, digestive gland extract, testes extract, ovary extract or combination of extracts of *Haliotis rufescens*. In one embodiment of the disclosed composition, the composition comprises from 20% to 50% of a whole body extract, visceral extract, conical appendage extract, digestive gland extract, testes extract, ovary extract or combination of extracts of *Haliotis rufescens*.

In one embodiment of the disclosed composition, the composition comprises from 1% to 100% of a whole body extract, visceral extract, conical appendage extract, digestive gland extract, testes extract, ovary extract or combination of extracts of *Haliotis corrugata*. In one embodiment of the disclosed composition, the composition comprises from 10% to 100% of a whole body extract, visceral extract, conical appendage extract, digestive gland extract, testes extract, ovary extract or combination of extracts of *Haliotis corrugata*. In one embodiment of the disclosed composition, the composition comprises from 20% to 100% of a whole body extract, visceral extract, conical appendage extract, digestive gland extract, testes extract, ovary extract or combination of extracts of *Haliotis corrugata*. In one embodiment of the disclosed composition, the composition comprises from 20% to 80% of a whole body extract, visceral extract, conical appendage extract, digestive gland extract, testes extract, ovary extract or combination of extracts of *Haliotis corrugata*. In one embodiment of the disclosed composition, the composition comprises from 20% to 60% of a whole body extract, visceral extract, conical appendage extract, digestive gland extract, testes extract, ovary extract or combination of extracts of *Haliotis corrugata*. In one embodiment of the disclosed composition, the composition comprises from 20% to 55% of a whole body extract, visceral extract, conical appendage extract, digestive gland extract, testes extract, ovary extract or combination of extracts of *Haliotis corrugata*.

In one embodiment of the disclosed composition, the composition comprises from 1% to 100% of a whole body extract, visceral extract, conical appendage extract, digestive gland extract, testes extract, ovary extract or combination of extracts of *Haliotis kamtschatkana*. In one embodiment of the disclosed composition, the composition comprises from 20% to 100% of a whole body extract, visceral extract, conical appendage extract, digestive gland extract, testes extract, ovary extract or combination of extracts of *Haliotis kamtschatkana*. In one embodiment of the disclosed composition, the composition comprises from 40% to 100% of a whole body extract, visceral extract, conical appendage extract, digestive gland extract, testes extract, ovary extract or combination of extracts of *Haliotis kamtschatkana*. In one embodiment of the disclosed composition, the composition comprises from 60% to 100% of a whole body extract, visceral extract, conical appendage extract, digestive gland extract, testes extract, ovary extract or combination of extracts of *Haliotis kamtschatkana*. In one embodiment of the disclosed composition, the composition comprises from 10% to 80% of a whole body extract, visceral extract, conical appendage extract, digestive gland extract, testes extract, ovary extract or combination of extracts of *Haliotis kamtschatkana*. In one embodiment of the disclosed composition, the composition comprises from 10% to 60% of a whole body extract, visceral extract, conical appendage extract, digestive gland extract, testes extract, ovary extract or combination of extracts of *Haliotis kamtschatkana*. In one embodiment of the disclosed composition, the composition comprises from 10% to 40% of a whole body extract, visceral extract, conical appendage extract, digestive gland extract, testes extract, ovary extract or combination of extracts of *Haliotis kamtschatkana*. In one embodiment of the disclosed composition, the composition comprises from 10% to 30% of a whole body extract, visceral extract, conical appendage extract, digestive gland extract, testes extract, ovary extract or combination of extracts of *Haliotis kamtschatkana*.

In one embodiment of the disclosed composition, the composition comprises from 1% to 100% of a whole body extract, visceral extract, conical appendage extract, digestive gland extract, testes extract, ovary extract or combination of extracts of *Haliotis walallensis*. In one embodiment of the disclosed composition, the composition comprises from 10% to 100% of a whole body extract, visceral extract, conical appendage extract, digestive gland extract, testes extract, ovary extract or combination of extracts of *Haliotis walallensis*. In one embodiment of the disclosed composition, the composition comprises from 20% to 100% of a whole body extract, visceral extract, conical appendage extract, digestive gland extract, testes extract, ovary extract or combination of extracts of *Haliotis walallensis*. In one embodiment of the disclosed composition, the composition comprises from 40% to 100% of a whole body extract, visceral extract, conical appendage extract, digestive gland extract, testes extract, ovary extract or combination of extracts of *Haliotis walallensis*. In one embodiment of the disclosed composition, the composition comprises from 20% to 60% of a whole body extract, visceral extract, conical appendage extract, digestive gland extract, testes extract, ovary extract or combination of extracts of *Haliotis walallensis*. In one embodiment of the disclosed composition, the composition comprises from 20% to 80% of a whole body extract, visceral extract, conical appendage extract, digestive gland extract, testes extract, ovary extract or combination of extracts of *Haliotis walallensis*. In one embodiment of the disclosed composition, the composition comprises from 40% to 60% of a whole body extract, visceral extract, conical appendage extract, digestive gland extract, testes extract, ovary extract or combination of extracts of *Haliotis walallensis*.

In one embodiment of the disclosed composition, the composition comprises from 1% to 100% of a whole body extract, visceral extract, conical appendage extract, digestive gland extract, testes extract, ovary extract or combination of extracts of hybrid *Haliotis rufescens×Haliotis corrugata*. In one embodiment of the disclosed composition, the composition comprises from 10% to 100% of a whole body extract, visceral extract, conical appendage extract, digestive gland extract, testes extract, ovary extract or combination of extracts of hybrid *Haliotis rufescens×Haliotis corrugata*. In one embodiment of the disclosed composition, the composition comprises from 20% to 100% of a whole body extract, visceral extract, conical appendage extract, digestive gland extract, testes extract, ovary extract or combination of extracts of hybrid *Haliotis rufescens×Haliotis corrugata*. In one embodiment of the disclosed composition, the composition comprises from 40% to 100% of a whole body extract, visceral extract, conical appendage extract, digestive gland extract, testes extract, ovary extract or combination of extracts of hybrid *Haliotis rufescens×Haliotis corrugata*. In one embodiment of the disclosed composition, the composition comprises from 10% to 80% of a whole body extract, visceral extract, conical appendage extract, digestive gland extract, testes extract, ovary extract or combination of extracts of hybrid *Haliotis rufescens×Haliotis corrugata*. In one embodiment of the disclosed composition, the composition comprises from 10% to 60% of a whole body extract, visceral extract, conical appendage extract, digestive gland extract, testes extract, ovary extract or combination of extracts of hybrid *Haliotis rufescens×Haliotis corrugata*. In one embodiment of the disclosed composition, the composition comprises from 10% to 50% of a whole body extract, visceral extract, conical appendage extract, digestive gland extract, testes extract, ovary extract or combination of extracts of hybrid *Haliotis rufescens×Haliotis corrugata*.

In one embodiment of the disclosed composition, the composition comprises from 1% to 100% of a whole body extract, visceral extract, conical appendage extract, digestive gland extract, testes extract, ovary extract or combination of extracts of hybrid *Haliotis rufescens×Haliotis fulgens*. In one embodiment of the disclosed composition, the composition comprises from 10% to 100% of a whole body extract, visceral extract, conical appendage extract, digestive gland extract, testes extract, ovary extract or combination of extracts of hybrid *Haliotis rufescens×Haliotis fulgens*. In one embodiment of the disclosed composition, the composition comprises from 20% to 100% of a whole body extract, visceral extract, conical appendage extract, digestive gland extract, testes extract, ovary extract or combination of extracts of hybrid *Haliotis rufescens×Haliotis fulgens*. In one embodiment of the disclosed composition, the composition comprises from 40% to 100% of a whole body extract, visceral extract, conical appendage extract, digestive gland extract, testes extract, ovary extract or combination of extracts of hybrid *Haliotis rufescens×Haliotis fulgens*. In one embodiment of the disclosed composition, the composition comprises from 10% to 80% of a whole body extract, visceral extract, conical appendage extract, digestive gland extract, testes extract, ovary extract or combination of extracts of hybrid *Haliotis rufescens×Haliotis fulgens*. In one embodiment of the disclosed composition, the composition comprises from 10% to 60% of a whole body extract, visceral extract, conical appendage extract, digestive gland extract, testes extract, ovary extract or combination of extracts of hybrid *Haliotis rufescens×Haliotis fulgens*. In one embodiment of the disclosed composition, the composition comprises from 10% to 50% of a whole body extract, visceral extract, conical appendage extract, digestive gland extract, testes extract, ovary extract or combination of extracts of hybrid *Haliotis rufescens×Haliotis fulgens*.

In one embodiment of the disclosed composition, the composition comprises from 1% to 100% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 10% to 100% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 20% to 100% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 40% to 100% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 10% to 80% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 10% to 60% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 10% to 50% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 25% to 60% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 25% to 80% of a whole body extract, visceral extract, conical appendage extract, digestive gland extract, testes extract, ovary extract or combination of extracts of hybrid *Haliotis rufescens×Haliotis laevagata*. In one embodiment of the disclosed composition, the composition comprises from 25% to 100% of a whole body extract, visceral extract, conical appendage extract, digestive gland extract, testes extract, ovary extract or combination of extracts of hybrid *Haliotis rufescens×Haliotis laevagata*.

Algae

Algae and seaweed peptides speed healing by promoting cell growth, nourishing the skin with vitamins and minerals and enhancing barrier function.

In one embodiment of the disclosed composition, the composition comprises from 1% to 100% of an extract of *Macrocystis integrifolia*. In one embodiment of the disclosed composition, the composition comprises from 1% to 80% of an extract of *Macrocystis integrifolia*. In one embodiment of the disclosed composition, the composition comprises from 1% to 60% of an extract of *Macrocystis integrifolia*. In one embodiment of the disclosed composition, the composition comprises from 1% to 40% of an extract of *Macrocystis integrifolia*. In one embodiment of the disclosed composition, the composition comprises from 10% to 80% of an extract of *Macrocystis integrifolia*. In one embodiment of the disclosed composition, the composition comprises from 20% to 60% of an extract of *Macrocystis integrifolia*. In one embodiment of the disclosed composition, the composition comprises from 20% to 40% of an extract of *Macrocystis integrifolia*.

In one embodiment of the disclosed composition, the composition comprises from 1% to 100% of an extract of *Macrocystis pyrifera*. In one embodiment of the disclosed composition, the composition comprises from 1% to 80% of an extract of *Macrocystis pyrifera*. In one embodiment of the disclosed composition, the composition comprises from 1% to 40% of an extract of *Macrocystis pyrifera*. In one embodiment of the disclosed composition, the composition comprises from 1% to 20% of an extract of *Macrocystis pyrifera*. In one embodiment of the disclosed composition, the composition comprises from 1% to 15% of an extract of *Macrocystis pyrifera*. In one embodiment of the disclosed composition, the composition comprises from 5% to 15% of an extract of *Macrocystis pyrifera*. In one embodiment of the disclosed composition, the composition comprises from 10% to 40% of an extract of *Macrocystis pyrifera*. In one embodiment of the disclosed composition, the composition comprises from 20% to 60% of an extract of *Macrocystis pyrifera*.

In one embodiment of the disclosed composition, the composition comprises from 1% to 100% of an extract of *Fucus vesiculosis*. In one embodiment of the disclosed composition, the composition comprises from 1% to 80% of an extract of *Fucus vesiculosis*. In one embodiment of the disclosed composition, the composition comprises from 1% to 50% of an extract of *Fucus vesiculosis*. In one embodiment of the disclosed composition, the composition comprises from 10% to 100% of an extract of *Fucus vesiculosis*. In one embodiment of the disclosed composition, the composition comprises from 20% to 80% of an extract of *Fucus vesiculosis*. In one embodiment of the disclosed composition, the composition comprises from 30% to 60% of an extract of *Fucus vesiculosis*. In one embodiment of the disclosed composition, the composition comprises from 40% to 50% of an extract of *Fucus vesiculosis*.

In one embodiment of the disclosed composition, the composition comprises from 1% to 100% of an extract of *Ascophyllum nodosum*. In one embodiment of the disclosed composition, the composition comprises from 1% to 80% of an extract of *Ascophyllum nodosum*. In one embodiment of the disclosed composition, the composition comprises from 1% to 60% of an extract of *Ascophyllum nodosum*. In one embodiment of the disclosed composition, the composition comprises from 1% to 40% of an extract of *Ascophyllum nodosum*. In one embodiment of the disclosed composition, the composition comprises from 1% to 20% of an extract of *Ascophyllum nodosum*. In one embodiment of the disclosed composition, the composition comprises from 1% to 10% of an extract of *Ascophyllum nodosum*. In one embodiment of the disclosed composition, the composition comprises from 5% to 10% of an extract of *Ascophyllum nodosum*. In one embodiment of the disclosed composition, the composition comprises from 10% to 80% of an extract of *Ascophyllum nodosum*. In one embodiment of the disclosed composition, the composition comprises from 20% to 60% of an extract of *Ascophyllum nodosum*. In one embodiment of the disclosed composition, the composition comprises from 30% to 50% of an extract of *Ascophyllum nodosum*.

In one embodiment of the disclosed composition, the composition comprises from 1% to 100% of an extract of *Spirulina pacifica*. In one embodiment of the disclosed composition, the composition comprises from 1% to 80% of an extract of *Spirulina pacifica*. In one embodiment of the disclosed composition, the composition comprises from 5% to 100% of an extract of *Spirulina pacifica*. In one embodiment of the disclosed composition, the composition comprises from 5% to 85% of an extract of *Spirulina pacifica*. In one embodiment of the disclosed composition, the composition comprises from 5% to 65% of an extract of *Spirulina pacifica*. In one embodiment of the disclosed composition, the composition comprises from 5% to 50% of an extract of *Spirulina pacifica*. In one embodiment of the disclosed composition, the composition comprises from 10% to 80% of an extract of *Spirulina pacifica*. In one embodiment of the disclosed composition, the composition comprises from 20% to 60% of an extract of *Spirulina pacifica*. In one embodiment of the disclosed composition, the composition comprises from 30% to 50% of an extract of *Spirulina pacifica*.

In one embodiment of the disclosed composition, the composition comprises from 1% to 100% of an extract of *Sargassum muticum*. In one embodiment of the disclosed composition, the composition comprises from 1% to 75% of an extract of *Sargassum muticum*. In one embodiment of the disclosed composition, the composition comprises from 1% to 50% of an extract of *Sargassum muticum*. In one embodiment of the disclosed composition, the composition comprises from 1% to 25% of an extract of *Sargassum muticum*. In one embodiment of the disclosed composition, the composition comprises from 5% to 25% of an extract of *Sargassum muticum*. In one embodiment of the disclosed composition, the composition comprises from 10% to 50% of an extract of *Sargassum muticum*. In one embodiment of the disclosed composition, the composition comprises from 20% to 60% of an extract of *Sargassum muticum*. In one embodiment of the disclosed composition, the composition comprises from 40% to 50% of an extract of *Sargassum muticum*. In one embodiment of the disclosed composition, the composition comprises from 25% to 75% of an extract of *Sargassum muticum*.

In one embodiment of the disclosed composition, the composition comprises from 1% to 100% of an extract of *Chlorella pyrenoidosa*. In one embodiment of the disclosed composition, the composition comprises from 5% to 80% of an extract of *Chlorella pyrenoidosa*. In one embodiment of the disclosed composition, the composition comprises from 5% to 60% of an extract of *Chlorella pyrenoidosa*. In one embodiment of the disclosed composition, the composition comprises from 5% to 40% of an extract of *Chlorella pyrenoidosa*. In one embodiment of the disclosed composition, the composition comprises from 10% to 80% of an extract of *Chlorella pyrenoidosa*. In one embodiment of the disclosed composition, the composition comprises from 20% to 60% of an extract of *Chlorella pyrenoidosa*. In one embodiment of the disclosed composition, the composition comprises from 30% to 50% of an extract of *Chlorella pyrenoidosa*.

In one embodiment of the disclosed composition, the composition comprises from 1% to 100% of an extract of *Chlorella variabilis*. In one embodiment of the disclosed composition, the composition comprises from 1% to 80% of an extract of *Chlorella variabilis*. In one embodiment of the disclosed composition, the composition comprises from 1% to 60% of an extract of *Chlorella variabilis*. In one embodiment of the disclosed composition, the composition comprises from 5% to 20% of an extract of *Chlorella variabilis*. In one embodiment of the disclosed composition, the composition comprises from 5% to 30% of an extract of *Chlorella variabilis*. In one embodiment of the disclosed composition, the composition comprises from 5% to 50% of an extract of *Chlorella variabilis*. In one embodiment of the disclosed composition, the composition comprises from 10% to 80% of an extract of *Chlorella variabilis*. In one embodiment of the disclosed composition, the composition comprises from 20% to 60% of an extract of *Chlorella variabilis*. In one embodiment of the disclosed composition, the composition comprises from 30% to 50% of an extract of *Chlorella variabilis*.

Cyanobacteria

In one embodiment of the disclosed composition, the composition comprises from 1% to 100% of an extract of *Spirulina pacifica*. In one embodiment of the disclosed composition, the composition comprises from 1% to 80% of an extract of *Spirulina pacifica*. In one embodiment of the disclosed composition, the composition comprises from 1% to 60% of an extract of *Spirulina pacifica*. In one embodiment of the disclosed composition, the composition comprises from 5% to 100% of an extract of *Spirulina pacifica*. In one embodiment of the disclosed composition, the composition comprises from 5% to 85% of an extract of *Spirulina pacifica*. In one embodiment of the disclosed composition, the composition comprises from 5% to 60% of an extract of *Spirulina pacifica*. In one embodiment of the disclosed composition, the composition comprises from 10% to 80% of an extract of *Spirulina pacifica*. In one embodiment of the disclosed composition, the composition comprises from 20% to 60% of an extract of *Spirulina pacifica*.

In one embodiment of the disclosed composition, the composition comprises from 1% to 100% of an extract of *Arthrospira maxima*. In one embodiment of the disclosed composition, the composition comprises from 1% to 80% of an extract of *Arthrospira maxima*. In one embodiment of the disclosed composition, the composition comprises from 1% to 60% of an extract of *Arthrospira maxima*. In one embodiment of the disclosed composition, the composition comprises from 5% to 25% of an extract of *Arthrospira maxima*. In one embodiment of the disclosed composition, the composition comprises from 5% to 50% of an extract of *Arthrospira maxima*. In one embodiment of the disclosed composition, the composition comprises from 5% to 75% of an extract of *Arthrospira maxima*. In one embodiment of the disclosed composition, the composition comprises from 10% to 80% of an extract of *Arthrospira maxima*. In one embodiment of the disclosed composition, the composition comprises from 20% to 60% of an extract of *Arthrospira maxima*. In one embodiment of the disclosed composition, the composition comprises from 30% to 50% of an extract of *Arthrospira maxima*.

In one embodiment of the disclosed composition, the composition comprises from 1% to 100% of an extract of *Arthrospira planensis*. In one embodiment of the disclosed composition, the composition comprises from 1% to 80% of an extract of *Arthrospira planensis*. In one embodiment of the disclosed composition, the composition comprises from 3% to 60% of an extract of *Arthrospira planensis*. In one embodiment of the disclosed composition, the composition comprises from 3% to 30% of an extract of *Arthrospira planensis*. In one embodiment of the disclosed composition, the composition comprises from 5% to 80% of an extract of *Arthrospira planensis*. In one embodiment of the disclosed composition, the composition comprises from 10% to 60% of an extract of *Arthrospira planensis*. In one embodiment of the disclosed composition, the composition comprises from 20% to 50% of an extract of *Arthrospira planensis*.

In one embodiment of the disclosed composition, the composition comprises from 1% to 100% of an extract of *Microcystis aeruginosa*. In one embodiment of the disclosed composition, the composition comprises from 1% to 80% of an extract of *Microcystis aeruginosa*. In one embodiment of the disclosed composition, the composition comprises from 1% to 50% of an extract of *Microcystis aeruginosa*. In one embodiment of the disclosed composition, the composition comprises from 1% to 30% of an extract of *Microcystis aeruginosa*. In one embodiment of the disclosed composition, the composition comprises from 1% to 20% of an extract of *Microcystis aeruginosa*. In one embodiment of the disclosed composition, the composition comprises from 1% to 10% of an extract of *Microcystis aeruginosa*. In one embodiment of the disclosed composition, the composition comprises from 5% to 10% of an extract of *Microcystis aeruginosa*. In one embodiment of the disclosed composition, the composition comprises from 5% to 20% of an extract of *Microcystis aeruginosa*. In one embodiment of the disclosed composition, the composition comprises from 5% to 30% of an extract of *Microcystis aeruginosa*.

In one embodiment of the disclosed composition, the composition comprises from 1% to 100% of an extract of *Microcystis wesenbergii*. In one embodiment of the disclosed composition, the composition comprises from 1% to 60% of an extract of *Microcystis wesenbergii*. In one embodiment of the disclosed composition, the composition comprises from 1% to 40% of an extract of *Microcystis wesenbergii*. In one embodiment of the disclosed composition, the composition comprises from 1% to 20% of an extract of *Microcystis wesenbergii*. In one embodiment of the disclosed composition, the composition comprises from 5% to 20% of an extract of *Microcystis wesenbergii*. In one embodiment of the disclosed composition, the composition comprises from 5% to 15% of an extract of *Microcystis wesenbergii*. In one embodiment of the disclosed composition, the composition comprises from 5% to 10% of an extract of *Microcystis wesenbergii*.

Bivalves

In one embodiment of the disclosed composition, the composition comprises from 1% to 100% of a whole body extract, visceral extract, gonad extract, testes extract, ovary extract or combination of extracts of *Chlamys rubida*. In one embodiment of the disclosed composition, the composition comprises from 1% to 80% of a whole body extract, visceral extract, gonad extract, testes extract, ovary extract or combination of extracts of *Chlamys rubida*. In one embodiment of the disclosed composition, the composition comprises from 1% to 60% of a whole body extract, visceral extract, gonad extract, testes extract, ovary extract or combination of extracts of *Chlamys rubida*. In one embodiment of the disclosed composition, the composition comprises from 1% to 40% of a whole body extract, visceral extract, gonad extract, testes extract, ovary extract or combination of extracts of *Chlamys rubida*. In one embodiment of the disclosed composition, the composition comprises from 5% to 40% of a whole body extract, visceral extract, gonad extract, testes extract, ovary extract or combination of extracts of *Chlamys rubida*. In one embodiment of the disclosed composition, the composition comprises from 10% to 40% of a whole body extract, visceral extract, gonad extract, testes extract, ovary extract or combination of extracts of *Chlamys rubida*. In one embodiment of the disclosed composition, the composition comprises from 10% to 80% of a whole body extract, visceral extract, gonad extract, testes extract, ovary extract or combination of extracts of *Chlamys rubida*. In one embodiment of the disclosed composition, the composition comprises from 20% to 60% of a whole body extract, visceral extract, gonad extract, testes extract, ovary extract or combination of extracts of *Chlamys rubida*.

In one embodiment of the disclosed composition, the composition comprises from 1% to 100% of a whole body extract, visceral extract, gonad extract, testes extract, ovary extract or combination of extracts of *Chlamys hastate*. In one embodiment of the disclosed composition, the composition comprises from 1% to 60% of a whole body extract, visceral extract, gonad extract, testes extract, ovary extract or combination of extracts of *Chlamys hastate*. In one embodiment of the disclosed composition, the composition comprises from 3% to 40% of a whole body extract, visceral extract, gonad extract, testes extract, ovary extract or combination of extracts of *Chlamys hastate*. In one embodiment of the disclosed composition, the composition comprises from 3% to 20% of a whole body extract, visceral extract, gonad extract, testes extract, ovary extract or combination of extracts of *Chlamys hastate*. In one embodiment of the disclosed composition, the composition comprises from 5% to 20% of a whole body extract, visceral extract, gonad extract, testes extract, ovary extract or combination of extracts of *Chlamys hastate*. In one embodiment of the disclosed composition, the composition comprises from 10% to 20% of a whole body extract, visceral extract, gonad extract, testes extract, ovary extract or combination of extracts of *Chlamys hastate*. In one embodiment of the disclosed composition, the composition comprises from 10% to 40% of a whole body extract, visceral extract, gonad extract, testes extract, ovary extract or combination of extracts of *Chlamys hastate*. In one embodiment of the disclosed composition, the composition comprises from 10% to 60% of a whole body extract, visceral extract, gonad extract, testes extract, ovary extract or combination of extracts of *Chlamys hastate*. In one embodiment of the disclosed composition, the composition comprises from 20% to 40% of a whole body extract, visceral extract, gonad extract, testes extract, ovary extract or combination of extracts of *Chlamys hastate*. In one embodiment of the disclosed composition, the composition comprises from 30% to 50% of a whole body extract, visceral extract, gonad extract, testes extract, ovary extract or combination of extracts of *Chlamys hastate*.

In one embodiment of the disclosed composition, the composition comprises from 1% to 100% of a whole body extract, visceral extract, gonad extract, testes extract, ovary extract or combination of extracts of *Crassotrea gigas*. In one embodiment of the disclosed composition, the composition comprises from 5% to 80% of a whole body extract, visceral extract, gonad extract, testes extract, ovary extract or combination of extracts of *Crassotrea gigas*. In one embodiment of the disclosed composition, the composition comprises from 5% to 60% of a whole body extract, visceral extract, gonad extract, testes extract, ovary extract or combination of extracts of *Crassotrea gigas*. In one embodiment of the disclosed composition, the composition comprises from 5% to 50% of a whole body extract, visceral extract, gonad extract, testes extract, ovary extract or combination of extracts of *Crassotrea gigas*. In one embodiment of the disclosed composition, the composition comprises from 10% to 50% of a whole body extract, visceral extract, gonad extract, testes extract, ovary extract or combination of extracts of *Crassotrea gigas*. In one embodiment of the disclosed composition, the composition comprises from 20% to 50% of a whole body extract, visceral extract, gonad extract, testes extract, ovary extract or combination of extracts of *Crassotrea gigas*. In one embodiment of the disclosed composition, the composition comprises from 30% to 50% of a whole body extract, visceral extract, gonad extract, testes extract, ovary extract or combination of extracts of *Crassotrea gigas*. In one embodiment of the disclosed composition, the composition comprises from 40% to 50% of a whole body extract, visceral extract, gonad extract, testes extract, ovary extract or combination of extracts of *Crassotrea gigas*.

In one embodiment of the disclosed composition, the composition comprises from 1% to 100% of a whole body extract, visceral extract, gonad extract, testes extract, ovary extract or combination of extracts of *Crassotrea corteziensis*. In one embodiment of the disclosed composition, the composition comprises from 5% to 80% of a whole body extract, visceral extract, gonad extract, testes extract, ovary extract or combination of extracts of *Crassotrea corteziensis*. In one embodiment of the disclosed composition, the composition comprises from 10% to 50% of a whole body extract, visceral extract, gonad extract, testes extract, ovary extract or combination of extracts of *Crassotrea corteziensis*. In one embodiment of the disclosed composition, the composition comprises from 10% to 30% of a whole body extract, visceral extract, gonad extract, testes extract, ovary extract or combination of extracts of *Crassotrea corteziensis*. In one embodiment of the disclosed composition, the composition comprises from 3% to 15% of a whole body extract, visceral extract, gonad extract, testes extract, ovary extract or combination of extracts of *Crassotrea corteziensis*. In one embodiment of the disclosed composition, the composition comprises from 5% to 15% of a whole body extract, visceral extract, gonad extract, testes extract, ovary extract or combination of extracts of *Crassotrea corteziensis*. In one embodiment of the disclosed composition, the composition comprises from 10% to 15% of a whole body extract, visceral extract, gonad extract, testes extract, ovary extract or combination of extracts of *Crassotrea corteziensis*.

In one embodiment of the disclosed composition, the composition comprises from 1% to 100% of a whole body extract, visceral extract, gonad extract, testes extract, ovary extract or combination of extracts of *Crassotrea columbiensis*. In one embodiment of the disclosed composition, the composition comprises from 1% to 80% of a whole body extract, visceral extract, gonad extract, testes extract, ovary extract or combination of extracts of *Crassotrea columbiensis*. In one embodiment of the disclosed composition, the composition comprises from 1% to 60% of a whole body extract, visceral extract, gonad extract, testes extract, ovary extract or combination of extracts of *Crassotrea columbiensis*. In one embodiment of the disclosed composition, the composition comprises from 1% to 40% of a whole body extract, visceral extract, gonad extract, testes extract, ovary extract or combination of extracts of *Crassotrea columbiensis*. In one embodiment of the disclosed composition, the composition comprises from 1% to 20% of a whole body extract, visceral extract, gonad extract, testes extract, ovary extract or combination of extracts of *Crassotrea columbiensis*. In one embodiment of the disclosed composition, the composition comprises from 5% to 10% of a whole body extract, visceral extract, gonad extract, testes extract, ovary extract or combination of extracts of *Crassotrea columbiensis*. In one embodiment of the disclosed composition, the composition comprises from 10% to 30% of a whole body extract, visceral extract, gonad extract, testes extract, ovary extract or combination of extracts of *Crassotrea columbiensis*. In one embodiment of the disclosed composition, the composition comprises from 20% to 50% of a whole body extract, visceral extract, gonad extract, testes extract, ovary extract or combination of extracts of *Crassotrea columbiensis*.

Sea Cucumbers

In one embodiment of the disclosed composition, the composition comprises from 1% to 100% of a whole body extract, visceral extract, gonad extract, testes extract, ovary extract or combination of extracts of *Holothuria mexicana*. In one embodiment of the disclosed composition, the composition comprises from 10% to 100% of a whole body extract, visceral extract, gonad extract, testes extract, ovary extract or combination of extracts of *Holothuria mexicana*. In one embodiment of the disclosed composition, the composition comprises from 20% to 100% of a whole body extract, visceral extract, gonad extract, testes extract, ovary extract or combination of extracts of *Holothuria mexicana*. In one embodiment of the disclosed composition, the composition comprises from 40% to 100% of a whole body extract, visceral extract, gonad extract, testes extract, ovary extract or combination of extracts of *Holothuria mexicana*. In one embodiment of the disclosed composition, the composition comprises from 60% to 100% of a whole body extract, visceral extract, gonad extract, testes extract, ovary extract or combination of extracts of *Holothuria mexicana*. In one embodiment of the disclosed composition, the composition comprises from 80% to 100% of a whole body extract, visceral extract, gonad extract, testes extract, ovary extract or combination of extracts of *Holothuria mexicana*. In one embodiment of the disclosed composition, the composition comprises from 20% to 80% of a whole body extract, visceral extract, gonad extract, testes extract, ovary extract or combination of extracts of *Holothuria mexicana*. In one embodiment of the disclosed composition, the composition comprises from 30% to 60% of a whole body extract, visceral extract, gonad extract, testes extract, ovary extract or combination of extracts of *Holothuria mexicana*. In one embodiment of the disclosed composition, the composition comprises from 40% to 50% of a whole body extract, visceral extract, gonad extract, testes extract, ovary extract or combination of extracts of *Holothuria mexicana*.

In one embodiment of the disclosed composition, the composition comprises from 1% to 100% of a whole body extract, visceral extract, gonad extract, testes extract, ovary extract or combination of extracts of *Holothuria californicus*. In one embodiment of the disclosed composition, the composition comprises from 5% to 80% of a whole body extract, visceral extract, gonad extract, testes extract, ovary extract or combination of extracts of *Holothuria californicus*. In one embodiment of the disclosed composition, the composition comprises from 10% to 60% of a whole body extract, visceral extract, gonad extract, testes extract, ovary extract or combination of extracts of *Holothuria californicus*. In one embodiment of the disclosed composition, the composition comprises from 10% to 40% of a whole body extract, visceral extract, gonad extract, testes extract, ovary extract or combination of extracts of *Holothuria californicus*. In one embodiment of the disclosed composition, the composition comprises from 15% to 40% of a whole body extract, visceral extract, gonad extract, testes extract, ovary extract or combination of extracts of *Holothuria californicus*. In one embodiment of the disclosed composition, the composition comprises from 20% to 40% of a whole body extract, visceral extract, gonad extract, testes extract, ovary extract or combination of extracts of *Holothuria californicus*. In one embodiment of the disclosed composition, the composition comprises from 30% to 40% of a whole body extract, visceral extract, gonad extract, testes extract, ovary extract or combination of extracts of *Holothuria californicus*. In one embodiment of the disclosed composition, the composition comprises from 20% to 80% of a whole body extract, visceral extract, gonad extract, testes extract, ovary extract or combination of extracts of *Holothuria californicus*. In one embodiment of the disclosed composition, the composition comprises from 30% to 60% of a whole body extract, visceral extract, gonad extract, testes extract, ovary extract or combination of extracts of *Holothuria californicus*. In one embodiment of the disclosed composition, the composition comprises from 40% to 50% of a whole body extract, visceral extract, gonad extract, testes extract, ovary extract or combination of extracts of *Holothuria californicus*.

In one embodiment of the disclosed composition, the composition comprises from 1% to 100% of a whole body extract, visceral extract, gonad extract, testes extract, ovary extract or combination of extracts of *Holothuria scabra*. In one embodiment of the disclosed composition, the composition comprises from 1% to 80% of a whole body extract, visceral extract, gonad extract, testes extract, ovary extract or combination of extracts of *Holothuria scabra*. In one embodiment of the disclosed composition, the composition comprises from 5% to 60% of a whole body extract, visceral extract, gonad extract, testes extract, ovary extract or combination of extracts of *Holothuria scabra*. In one embodiment of the disclosed composition, the composition comprises from 10% to 60% of a whole body extract, visceral extract, gonad extract, testes extract, ovary extract or combination of extracts of *Holothuria scabra*. In one embodiment of the disclosed composition, the composition comprises from 10% to 40% of a whole body extract, visceral extract, gonad extract, testes extract, ovary extract or combination of extracts of *Holothuria scabra*. In one embodiment of the disclosed composition, the composition comprises from 10% to 20% of a whole body extract, visceral extract, gonad extract, testes extract, ovary extract or combination of extracts of *Holothuria scabra*. In one embodiment of the disclosed composition, the composition comprises from 20% to 50% of a whole body extract, visceral extract, gonad extract, testes extract, ovary extract or combination of extracts of *Holothuria scabra*. In one embodiment of the disclosed composition, the composition comprises from 30% to 60% of a whole body extract, visceral extract, gonad extract, testes extract, ovary extract or combination of extracts of *Holothuria scabra*.

In one embodiment of the disclosed composition, the composition comprises from 1% to 100% of a whole body extract, visceral extract, gonad extract, testes extract, ovary extract or combination of extracts of *Stichopus chlorontus*. In one embodiment of the disclosed composition, the composition comprises from 1% to 80% of a whole body extract, visceral extract, gonad extract, testes extract, ovary extract or combination of extracts of *Stichopus chlorontus*. In one embodiment of the disclosed composition, the composition comprises from 5% to 60% of a whole body extract, visceral extract, gonad extract, testes extract, ovary extract or combination of extracts of *Stichopus chlorontus*. In one embodiment of the disclosed composition, the composition comprises from 5% to 50% of a whole body extract, visceral extract, gonad extract, testes extract, ovary extract or combination of extracts of *Stichopus chlorontus*. In one embodiment of the disclosed composition, the composition comprises from 10% to 50% of a whole body extract, visceral extract, gonad extract, testes extract, ovary extract or combination of extracts of *Stichopus chlorontus*. In one embodiment of the disclosed composition, the composition comprises from 20% to 50% of a whole body extract, visceral extract, gonad extract, testes extract, ovary extract or combination of extracts of *Stichopus chlorontus*. In one embodiment of the disclosed composition, the composition comprises from 30% to 50% of a whole body extract, visceral extract, gonad extract, testes extract, ovary extract or combination of extracts of *Stichopus chlorontus*. In one embodiment of the disclosed composition, the composition comprises from 40% to 50% of a whole body extract, visceral extract, gonad extract, testes extract, ovary extract or combination of extracts of *Stichopus chlorontus*.

In one embodiment of the disclosed composition, the composition comprises from 1% to 100% of a whole body extract, visceral extract, gonad extract, testes extract, ovary extract or combination of extracts of *Stichopus horrens*. In one embodiment of the disclosed composition, the composition comprises from 1% to 80% of a whole body extract, visceral extract, gonad extract, testes extract, ovary extract or combination of extracts of *Stichopus horrens*. In one embodiment of the disclosed composition, the composition comprises from 1% to 60% of a whole body extract, visceral extract, gonad extract, testes extract, ovary extract or combination of extracts of *Stichopus horrens*. In one embodiment of the disclosed composition, the composition comprises from 5% to 50% of a whole body extract, visceral extract, gonad extract, testes extract, ovary extract or combination of extracts of *Stichopus horrens*. In one embodiment of the disclosed composition, the composition comprises from 5% to 40% of a whole body extract, visceral extract, gonad extract, testes extract, ovary extract or combination of extracts of *Stichopus horrens*. In one embodiment of the disclosed composition, the composition comprises from 5% to 35% of a whole body extract, visceral extract, gonad extract, testes extract, ovary extract or combination of extracts of *Stichopus horrens*. In one embodiment of the disclosed composition, the composition comprises from 10% to 35% of a whole body extract, visceral extract, gonad extract, testes extract, ovary extract or combination of extracts of *Stichopus horrens*. In one embodiment of the disclosed composition, the composition comprises from 15% to 35% of a whole body extract, visceral extract, gonad extract, testes extract, ovary extract or combination of extracts of *Stichopus horrens*. In one embodiment of the disclosed composition, the composition comprises from 20% to 35% of a whole body extract, visceral extract, gonad extract, testes extract, ovary extract or combination of extracts of *Stichopus horrens*.

In one embodiment of the disclosed composition, the composition comprises from 1% to 100% of a whole body extract, visceral extract, gonad extract, testes extract, ovary extract or combination of extracts of *Stichopus japonicus*. In one embodiment of the disclosed composition, the composition comprises from 1% to 80% of a whole body extract, visceral extract, gonad extract, testes extract, ovary extract or combination of extracts of *Stichopus japonicus*. In one embodiment of the disclosed composition, the composition comprises from 5% to 60% of a whole body extract, visceral extract, gonad extract, testes extract, ovary extract or combination of extracts of *Stichopus japonicus*. In one embodiment of the disclosed composition, the composition comprises from 5% to 40% of a whole body extract, visceral extract, gonad extract, testes extract, ovary extract or combination of extracts of *Stichopus japonicus*. In one embodiment of the disclosed composition, the composition comprises from 5% to 25% of a whole body extract, visceral extract, gonad extract, testes extract, ovary extract or combination of extracts of *Stichopus japonicus*. In one embodiment of the disclosed composition, the composition comprises from 10% to 25% of a whole body extract, visceral extract, gonad extract, testes extract, ovary extract or combination of extracts of *Stichopus japonicus*. In one embodiment of the disclosed composition, the composition comprises from 15% to 25% of a whole body extract, visceral extract, gonad extract, testes extract, ovary extract or combination of extracts of *Stichopus japonicus*.

In one embodiment of the disclosed composition, the composition comprises from 1% to 100% of a whole body extract, visceral extract, gonad extract, testes extract, ovary extract or combination of extracts of *Apostichopus japonicus*. In one embodiment of the disclosed composition, the composition comprises from 1% to 80% of a whole body extract, visceral extract, gonad extract, testes extract, ovary extract or combination of extracts of *Apostichopus japonicus*. In one embodiment of the disclosed composition, the composition comprises from 5% to 60% of a whole body extract, visceral extract, gonad extract, testes extract, ovary extract or combination of extracts of *Apostichopus japonicus*. In one embodiment of the disclosed composition, the composition comprises from 5% to 40% of a whole body extract, visceral extract, gonad extract, testes extract, ovary extract or combination of extracts of *Apostichopus japonicus*. In one embodiment of the disclosed composition, the composition comprises from 5% to 25% of a whole body extract, visceral extract, gonad extract, testes extract, ovary extract or combination of extracts of *Apostichopus japonicus*. In one embodiment of the disclosed composition, the composition comprises from 10% to 25% of a whole body extract, visceral extract, gonad extract, testes extract, ovary extract or combination of extracts of *Apostichopus japonicus*. In one embodiment of the disclosed composition, the composition comprises from 15% to 25% of a whole body extract, visceral extract, gonad extract, testes extract, ovary extract or combination of extracts of *Apostichopus japonicus*.

In one embodiment of the disclosed composition, the composition comprises from 1% to 100% of a whole body extract, visceral extract, gonad extract, testes extract, ovary extract or combination of extracts a visceral extract of *Cucumaria japonica*. In one embodiment of the disclosed composition, the composition comprises from 1% to 80% of a whole body extract, visceral extract, gonad extract, testes extract, ovary extract or combination of extracts a visceral extract of *Cucumaria japonica*. In one embodiment of the disclosed composition, the composition comprises from 5% to 60% of a whole body extract, visceral extract, gonad extract, testes extract, ovary extract or combination of extracts a visceral extract of *Cucumaria japonica*. In one embodiment of the disclosed composition, the composition comprises from 10% to 60% of a whole body extract, visceral extract, gonad extract, testes extract, ovary extract or combination of extracts a visceral extract of *Cucumaria japonica*. In one embodiment of the disclosed composition, the composition comprises from 15% to 60% of a whole body extract, visceral extract, gonad extract, testes extract, ovary extract or combination of extracts a visceral extract of *Cucumaria japonica*. In one embodiment of the disclosed composition, the composition comprises from 25% to 60% of a whole body extract, visceral extract, gonad extract, testes extract, ovary extract or combination of extracts a visceral extract of *Cucumaria japonica*. In one embodiment of the disclosed composition, the composition comprises from 30% to 50% of a whole body extract, visceral extract, gonad extract, testes extract, ovary extract or combination of extracts a visceral extract of *Cucumaria japonica*. In one embodiment of the disclosed composition, the composition comprises from 20% to 40% of a whole body extract, visceral extract, gonad extract, testes extract, ovary extract or combination of extracts a visceral extract of *Cucumaria japonica*. In one embodiment of the disclosed composition, the composition comprises from 15% to 30% of a whole body extract, visceral extract, gonad extract, testes extract, ovary extract or combination of extracts a visceral extract of *Cucumaria japonica*.

Crustaceans

In one embodiment of the disclosed composition, the composition comprises from 1% to 100% of a whole body extract, visceral extract, gonad extract, testes extract, ovary extract or combination of extracts of *Paralothodes camtschaticus*. In one embodiment of the disclosed composition, the composition comprises from 1% to 80% of a whole body extract, visceral extract, gonad extract, testes extract, ovary extract or combination of extracts of *Paralothodes camtschaticus*. In one embodiment of the disclosed composition, the composition comprises from 5% to 60% of a whole body extract, visceral extract, gonad extract, testes extract, ovary extract or combination of extracts of *Paralothodes camtschaticus*. In one embodiment of the disclosed composition, the composition comprises from 5% to 50% of a whole body extract, visceral extract, gonad extract, testes extract, ovary extract or combination of extracts of *Paralothodes camtschaticus*. In one embodiment of the disclosed composition, the composition comprises from 10% to 50% of a whole body extract, visceral extract, gonad extract, testes extract, ovary extract or combination of extracts of *Paralothodes camtschaticus*. In one embodiment of the disclosed composition, the composition comprises from 25% to 50% of a whole body extract, visceral extract, gonad extract, testes extract, ovary extract or combination of extracts of *Paralothodes camtschaticus*. In one embodiment of the disclosed composition, the composition comprises from 15% to 40% of a whole body extract, visceral extract, gonad extract, testes extract, ovary extract or combination of extracts of *Paralothodes camtschaticus*. In one embodiment of the disclosed composition, the composition comprises from 15% to 25% of a whole body extract, visceral extract, gonad extract, testes extract, ovary extract or combination of extracts of *Paralothodes camtschaticus*. In one embodiment of the disclosed composition, the composition comprises from 10% to 25% of a whole body extract, visceral extract, gonad extract, testes extract, ovary extract or combination of extracts of *Paralothodes camtschaticus*.

Additional embodiments are described in the following paragraphs.

Paragraph 1. A composition comprising an abalone tissue extract.

Paragraph 2. The composition of Paragraph 1, wherein the abalone is *Haliotis* spp.

Paragraph 3. The composition of Paragraph 2, wherein the *Haliotis* spp. is selected from the group consisting of *Haliotis fulgens, Haliotis rufescens, Haliotis corrugata, Haliotis kamtschatkana*, and *Haliotis walallensis*.

Paragraph 4. The composition of Paragraph 1, wherein the abalone is a hybrid abalone.

Paragraph 5. The composition of Paragraph 4, wherein the hybrid abalone is selected from the group consisting of *Haliotis rufescens×Haliotis corrugate, Haliotis rufescens× Haliotis fulgens*, and *Haliotis rufescens×Haliotis laevagata*.

Paragraph 6. The composition of Paragraph 1, wherein the tissue is selected from the group consisting of at least one of muscle, viscera, conical appendage, digestive gland, gonad, testes and ovary.

Paragraph 7. The composition of Paragraph 1, further comprising an extract from a marine organism.

Paragraph 8. The composition of Paragraph 7, wherein the marine organism is selected from the group consisting of alga, bivalve, crustacean, sea cucumber, and cyanobacteria.

Paragraph 9. The composition of Paragraph 8, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa*, and *Chlorella variabilis*.

Paragraph 10. The composition of Paragraph 8, wherein the bivalve is selected from the group consisting of *Chlamys rubida, Chlamys hastate, Crassotrea gigas, Crassotrea corteziensis*, and *Crassotrea columbiensis*.

Paragraph 11. The composition of Paragraph 8, wherein the crustacean is *Paralothodes camtschaticus*.

Paragraph 12. The composition of Paragraph 8, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus*, and *Cucumaria japonica*.

Paragraph 13. The composition of Paragraph 8, wherein the cyanobacteria is selected from the group consisting of *Spirulina pacifica, Arthrospira maxima, Arthrospira planensis, Microcystis aeruginosa*, and *Microcystis wesenbergii*.

Paragraph 14. The composition of Paragraph 1, further comprising a cosmetic product.

Paragraph 15. The composition of Paragraph 14, wherein the cosmetic product is selected from the group consisting of one or more of acetyl hexapeptide-3 (argirilene), acrylates/ $C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis, Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis, Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, *saccharomyces* ferment, *Salvia hispanica* (chia) seed oil, *Sclerocarya birrea* (marula) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Paragraph 16. A composition comprising an alga tissue extract.

Paragraph 17. The composition of Paragraph 16, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa*, and *Chlorella variabilis*.

Paragraph 18. The composition of Paragraph 16, wherein the tissue is selected from the group consisting of at least one of frond and whole body.

Paragraph 19. The composition of Paragraph 16, further comprising an extract from a marine organism.

Paragraph 20. The composition of Paragraph 19, wherein the marine organism is selected from the group consisting of abalone, bivalve, crustacean, sea cucumber, and cyanobacteria.

Paragraph 21. The composition of Paragraph 20, wherein the abalone is *Haliotis* spp.

Paragraph 22. The composition of Paragraph 21, wherein the *Haliotis* spp. is selected from the group consisting of *Haliotis fulgens, Haliotis rufescens, Haliotis corrugata, Haliotis kamtschatkana*, and *Haliotis walallensis*.

Paragraph 23. The composition of Paragraph 20, wherein the abalone is a hybrid abalone.

Paragraph 24. The composition of Paragraph 23, wherein the hybrid abalone is selected from the group consisting of *Haliotis rufescens×Haliotis corrugate, Haliotis rufescens× Haliotis fulgens*, and *Haliotis rufescens×Haliotis laevagata*.

Paragraph 25. The composition of Paragraph 20, wherein the bivalve is selected from the group consisting of *Chlamys rubida, Chlamys hastate, Crassotrea gigas, Crassotrea corteziensis*, and *Crassotrea columbiensis*.

Paragraph 26. The composition of Paragraph 20, wherein the crustacean is *Paralothodes camtschaticus*.

Paragraph 27. The composition of Paragraph 20, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus*, and *Cucumaria japonica*.

Paragraph 28. The composition of Paragraph 20, wherein the cyanobacteria is selected from the group consisting of *Spirulina pacifica, Arthrospira maxima, Arthrospira planensis, Microcystis aeruginosa*, and *Microcystis wesenbergii*.

Paragraph 29. The composition of Paragraph 16, further comprising a cosmetic product.

Paragraph 30. The composition of Paragraph 29, wherein the cosmetic product is selected from the group consisting of one or more of acetyl hexapeptide-3 (argirilene), acrylates/ $C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis, Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis, Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, saccharomyces ferment, *Salvia hispanica* (chia) seed oil, *Sclerocarya birrea* (marula) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Paragraph 31. A composition comprising an bivalve tissue extract.

Paragraph 32. The composition of Paragraph 31, wherein the bivalve is selected from the group consisting of *Chlamys rubida, Chlamys hastate, Crassotrea gigas, Crassotrea corteziensis*, and *Crassotrea columbiensis*.

Paragraph 33. The composition of Paragraph 31, wherein the tissue is selected from the group consisting of at least one of adductor muscle, viscera, and gonad.

Paragraph 34. The composition of Paragraph 31, further comprising an extract from a marine organism.

Paragraph 35. The composition of Paragraph 34, wherein the marine organism is selected from the group consisting of abalone alga, crustacean, sea cucumber, and cyanobacteria.

Paragraph 36. The composition of Paragraph 35, wherein the abalone is *Haliotis* spp.

Paragraph 37. The composition of Paragraph 36, wherein the *Haliotis* spp. is selected from the group consisting of *Haliotis fulgens, Haliotis rufescens, Haliotis corrugata, Haliotis kamtschatkana*, and *Haliotis walallensis*.

Paragraph 38. The composition of Paragraph 35, wherein the abalone is a hybrid abalone.

Paragraph 39. The composition of Paragraph 38, wherein the hybrid abalone is selected from the group consisting of *Haliotis rufescens×Haliotis corrugate, Haliotis rufescens×Haliotis fulgens*, and *Haliotis rufescens×Haliotis laevagata*.

Paragraph 40. The composition of Paragraph 35, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa*, and *Chlorella variabilis*.

Paragraph 41. The composition of Paragraph 35, wherein the crustacean is *Paralothodes camtschaticus*.

Paragraph 42. The composition of Paragraph 35, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus*, and *Cucumaria japonica*.

Paragraph 43. The composition of Paragraph 35, wherein the cyanobacteria is selected from the group consisting of *Spirulina pacifica, Arthrospira maxima, Arthrospira planensis, Microcystis aeruginosa*, and *Microcystis wesenbergii*.

Paragraph 44. The composition of Paragraph 31, further comprising a cosmetic product.

Paragraph 45. The composition of Paragraph 44, wherein the cosmetic product is selected from the group consisting of one or more of acetyl hexapeptide-3 (argirilene), acrylates/$C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis, Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis, Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, saccharomyces ferment, *Salvia hispanica* (chia) seed oil, *Sclerocarya birrea* (marula) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Paragraph 46. A composition comprising a crustacean tissue extract.

Paragraph 47. The composition of Paragraph 46, wherein the crustacean is *Paralothodes camtschaticus*.

Paragraph 48. The composition of Paragraph 46, wherein the tissue is selected from the group consisting of at least one of exoskeleton, muscle, viscera, and gonad.

Paragraph 49. The composition of Paragraph 46, further comprising an extract from a marine organism.

Paragraph 50. The composition of Paragraph 49, wherein the marine organism is selected from the group consisting of abalone, alga, bivalve, sea cucumber, and cyanobacteria.

Paragraph 51. The composition of Paragraph 50, wherein the abalone is *Haliotis* spp.

Paragraph 52. The composition of Paragraph 51, wherein the *Haliotis* spp. is selected from the group consisting of *Haliotis fulgens, Haliotis rufescens, Haliotis corrugata, Haliotis kamtschatkana,* and *Haliotis walallensis.*

Paragraph 53. The composition of Paragraph 50, wherein the abalone is a hybrid abalone.

Paragraph 54. The composition of Paragraph 53, wherein the hybrid abalone is selected from the group consisting of *Haliotis rufescens*×*Haliotis corrugate, Haliotis rufescens*× *Haliotis fulgens,* and *Haliotis rufescens*×*Haliotis laevagata.*

Paragraph 55. The composition of Paragraph 50, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa,* and *Chlorella variabilis.*

Paragraph 56. The composition of Paragraph 50, wherein the bivalve is selected from the group consisting of *Chlamys rubida, Chlamys hastate, Crassotrea gigas, Crassotrea corteziensis,* and *Crassotrea columbiensis.*

Paragraph 57. The composition of Paragraph 50, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus,* and *Cucumaria japonica.*

Paragraph 58. The composition of Paragraph 50, wherein the cyanobacteria is selected from the group consisting of *Spirulina pacifica, Arthrospira maxima, Arthrospira planensis, Microcystis aeruginosa,* and *Microcystis wesenbergii.*

Paragraph 59. The composition of Paragraph 46, further comprising a cosmetic product.

Paragraph 60. The composition of Paragraph 59, wherein the cosmetic product is selected from the group consisting of one or more of acetyl hexapeptide-3 (argirilene), acrylates/ $C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis, Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis, Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, saccharomyces ferment, *Salvia hispanica* (chia) seed oil, *Sclerocarya birrea* (marula) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Paragraph 61. A composition comprising a sea cucumber tissue extract.

Paragraph 62. The composition of Paragraph 61, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus,* and *Cucumaria japonica.*

Paragraph 63. The composition of Paragraph 61, wherein the tissue is selected from the group consisting of at least one of body wall, muscle, viscera, and gonad.

Paragraph 64. The composition of Paragraph 61, further comprising an extract from a marine organism.

Paragraph 65. The composition of Paragraph 64, wherein the marine organism is selected from the group consisting of abalone alga, bivalve, crustacean, and cyanobacteria.

Paragraph 66. The composition of Paragraph 65, wherein the abalone is *Haliotis* spp.

Paragraph 67. The composition of Paragraph 66, wherein the *Haliotis* spp. is selected from the group consisting of *Haliotis fulgens, Haliotis rufescens, Haliotis corrugata, Haliotis kamtschatkana,* and *Haliotis walallensis.*

Paragraph 68. The composition of Paragraph 65, wherein the abalone is a hybrid abalone.

Paragraph 69. The composition of Paragraph 68, wherein the hybrid abalone is selected from the group consisting of *Haliotis rufescens*×*Haliotis corrugate, Haliotis rufescens*× *Haliotis fulgens,* and *Haliotis rufescens*×*Haliotis laevagata.*

Paragraph 70. The composition of Paragraph 65, wherein the alga is selected from the group consisting of *Macrocystis integrifolia, Macrocystis pyrifera, Fucus vesiculosis,*

*Ascophyllum nodosum, Spirulina pacifica, Sargassum muticum, Chlorella pyrenoidosa*, and *Chlorella variabilis*.

Paragraph 71. The composition of Paragraph 65, wherein the bivalve is selected from the group consisting of *Chlamys rubida, Chlamys hastate, Crassotrea gigas, Crassotrea corteziensis*, and *Crassotrea columbiensis*.

Paragraph 72. The composition of Paragraph 65, wherein the crustacean is *Paralothodes camtschaticus*.

Paragraph 73. The composition of Paragraph 65, wherein the cyanobacteria is selected from the group consisting of *Spirulina pacifica, Arthrospira maxima, Arthrospira planensis, Microcystis aeruginosa*, and *Microcystis wesenbergii*.

Paragraph 74. The composition of Paragraph 61, further comprising a cosmetic product.

Paragraph 75. The composition of Paragraph 74, wherein the cosmetic product is selected from the group consisting of one or more of acetyl hexapeptide-3 (argirilene), acrylates/ $C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis, Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis, Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, saccharomyces ferment, *Salvia hispanica* (chia) seed oil, *Sclerocarya birrea* (marula) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Paragraph 76. A composition comprising an cyanobacteria extract.

Paragraph 77. The composition of Paragraph 76, wherein the cyanobacteria is selected from the group consisting of *Spirulina pacifica, Arthrospira maxima, Arthrospira planensis, Microcystis aeruginosa*, and *Microcystis wesenbergii*.

Paragraph 78. The composition of Paragraph 76, further comprising an extract from a marine organism.

Paragraph 79. The composition of Paragraph 78, wherein the marine organism is selected from the group consisting of alga, bivalve, crustacean, sea cucumber, and cyanobacteria.

Paragraph 80. The composition of Paragraph 79, wherein the abalone is *Haliotis* spp.

Paragraph 81. The composition of Paragraph 80, wherein the *Haliotis* spp. is selected from the group consisting of *Haliotis fulgens, Haliotis rufescens, Haliotis corrugata, Haliotis kamtschatkana*, and *Haliotis walallensis*.

Paragraph 82. The composition of Paragraph 79, wherein the abalone is a hybrid abalone.

Paragraph 83. The composition of Paragraph 82, wherein the hybrid abalone is selected from the group consisting of *Haliotis rufescens×Haliotis corrugate, Haliotis rufescens× Haliotis fulgens*, and *Haliotis rufescens×Haliotis laevagata*.

Paragraph 84. The composition of Paragraph 79, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa*, and *Chlorella variabilis*.

Paragraph 85. The composition of Paragraph 79 wherein the bivalve is selected from the group consisting of *Chlamys rubida, Chlamys hastate, Crassotrea gigas, Crassotrea corteziensis*, and *Crassotrea columbiensis*.

Paragraph 86. The composition of Paragraph 79 wherein the crustacean is *Paralothodes camtschaticus*.

Paragraph 87. The composition of Paragraph 79 wherein the sea cucumber is selected from the group consisting of *Holothuria mexicana, Holothuria californicus, Holothuria scabra, Stichopus chlorontus, Stichopus horrens, Stichopus japonicus, Apostichopus japonicus*, and *Cucumaria japonica*.

Paragraph 88. The composition of Paragraph 76, further comprising a cosmetic product.

Paragraph 89. The composition of Paragraph 88 wherein the cosmetic product is selected from the group consisting of one or more of acetyl hexapeptide-3 (argirilene), acrylates/ $C_{10-30}$ alkyl acrylate cross-polymer, *Actinidia deliciosa* (kiwi) seed oil, algae extract, *Andropogon zizanioides* (vetiver) essential oil, *Aniba rosaeodora* (rosewood) essential oil, apricot kernel oil, *Arctostaphylos uva ursi* extract, *Argania spinosa* (argan) oil, argirilene, astaxanthin, beta glucan, *Borago officinalis* (borage) oil, *Boswellia carterii* (frankincense) essential oil, *Caesalpinia spinosa* (tara) gum], calcium carbonate, *Camellia oleifera* (camellia) oil, *Camellia sinensis, Cannabis sativa* (hemp) seed oil, caprylic/capric triglyceride], *Carica papaya* (papaya) seed oil, cellulose gum, *Centella asiatica* (gotu kola) extract, ceramide 1, ceramide 3, ceramide 6 II, ceramide complex, cetearyl glucoside, chitin, chitosan, cholecalciferol (vitamin D3), cholesterol, *Citrullus lanatus* (watermelon) extract, *Citrus aurantium* (neroli) hydrosol, *Citrus paradisi* (grapefruit) essential oil, *Cocos nucifera* (coconut) oil, coenzyme Q10, *Crithmum maritimum* (sea fennel) extract, decyl polyglucoside, dipeptide diaminobutyroyl benzylamide diacetate (snake peptides), elastin, *Enteromorpha compressa* extract, fatty acids, gamma-oryzanol, geranylgeranone gga, gluconolactone, glucosamine, glycan booster [tetradecyl amino-butyroylvalyl-aminobutyric urea trifluoro-acetate, glycerin, *Glycine soja* (soybean) oil, glycoproteins, *Glycyrrhiza glabra* (licorice root) extract, green tea extract, *Gynostemma pentaphyllum* (gynostemma) extract, *Haematococcus pulvialis*, *Helianthus annuus* (sunflower) seed oil, homeostatine, hyaluronic acid, hydrolyzed rice bran extract, hydroquinone, lactoceramides, *Lavendula angustfolia* (lavender) essential oil, lecithin, *Leontopodium alpinum* (edelweiss) extract, leuconostoc/radish root ferment (leucidal), linoleic acid, magnesium ascorbyl phosphate, magnesium chloride, matrix peptides, mixed tocopherols (vitamin E), *Morus alba* (mulberry) root extract, niacinamide, noni, non-nano zinc oxide, oat beta glucans, *Oenothera biennis* (evening primrose) oil, oleic acid, omega 6 fatty acids, omega 9 fatty acids, omega-3 fatty acids, *Oryza sativa* (rice) bran oil, palmitic, palmitoyl tripeptide-5, *Passiflora incarnate* (passion fruit) oil, pearl powder, *Persea gratissima* (avocado) oil, phytosphingosine, *Pinus densiflora* (red pine needle) oil, *Plantago* species (plantain) leaf extract, *Polianthes tuberosa* (tuberose) essential oil, polyaminopropyl biguanide (cosmocil CQ), polyglucose/lactylate, *Populus tremuloides* (aspen) bark extract, potassium sorbate, *Prunus armeniaca* (apricot) kernel oil, pullulan, red pond algae, red raspberry seed oil, resveratrol, retinyl palmitate (retinol), *Rosa centifolia* (rose) essential oil, *Rosa rubignosa* (rosehip) seed oil, *Rosmarinus officinalis* (rosemary) oleoresin, *Rubus idaeus* (red raspberry) seed oil, saccharomyces ferment, *Salvia hispanica* (chia) seed oil, *Sclerocarya birrea* (marula) oil, sea kelp extract, *Sesamum indicum* (sesame seed) oil, *Simmondsia chinensis* (jojoba) oil, SOD, sodium alginate, sodium benzoate, sodium hyaluronate, sodium lauroyl lactylate, soy peptides, soy-rice peptides [oxidoreductase], squalene, sucrose cocoate, sugar mulse [cetearyl alcohol], *Tamarindus indica* (tamarind) seed extract, teprenone, thioctic (alpha lipoic) acid, *Trachelospermum jasminoides* (star jasmine) essential oil, tripeptide-29, tripeptides, ubidecarenone, undecylenoyl phenylalanine, vitamin A, vitamin C, *Vitus viniferi* (grapeseed) oil, watermelon seed oil, white tea extract, xanthan gum, and xylitum black tea ferment (kombucha) extract.

Paragraph 90. A method of producing an abalone tissue extract, comprising the steps of: a) removing a tissue from an abalone,
b) breaking up the cells in the tissue,
c) adding a solvent,
d) separating the solvent fraction from a sediment fraction, and.
e) collecting the solvent fraction to obtain the abalone tissue extract.

Paragraph 91. The method of Paragraph 90, wherein the abalone is *Haliotis* spp.

Paragraph 92. The method of Paragraph 91, wherein the *Haliotis* spp. is selected from the group consisting of *Haliotis fulgens, Haliotis rufescens, Haliotis corrugata, Haliotis kamtschatkana*, and *Haliotis walallensis*.

Paragraph 93. The method of Paragraph 90, wherein the abalone is a hybrid abalone.

Paragraph 94. The method of Paragraph 93, wherein the hybrid abalone is selected from the group consisting of *Haliotis rufescens×Haliotis corrugate, Haliotis rufescens× Haliotis fulgens*, and *Haliotis rufescens×Haliotis laevagata*.

Paragraph 95. The method of Paragraph 90, wherein the tissue is selected from the group consisting of at least one of muscle, viscera, conical appendage, digestive gland, gonad, testes and ovary.

Paragraph 96. The method of Paragraph 90, wherein the solvent is selected from the group consisting of at least one of a polar solvent and a non-polar solvent.

Paragraph 97. The method of Paragraph 90, wherein the polar solvent is selected from the group consisting of at least one of dimethyl sulfoxide (DMSO), isopropyl alcohol, ethanol, methanol, acetic acid and water.

Paragraph 99. The method of Paragraph 90, wherein the non-polar solvent is selected from the group consisting of at least one of hexane, chloroform and ether.

Paragraph 99. The method of Paragraph 90, wherein the method of separating the solvent fraction from the sediment fraction is selected from the group consisting of by gravity, centrifugation, filtration, column chromatography, and HPLC.

Paragraph 100. The method of Paragraph 90, wherein the method of breaking up the cells in the tissue is selected from the group consisting of a blender, homogenizer, grinder, and mortar and pestle.

Paragraph 101. The method of Paragraph 90, further comprising step f) freeze drying the abalone tissue extract.

Paragraph 102. The method of Paragraph 90, further comprising step f) lyophilizing the abalone tissue extract.

Paragraph 103. The method of Paragraph 90, wherein between step a) and step b) further comprising step 1) freezing the tissue.

Paragraph 104. The method of Paragraph 90, wherein between step a) and step b) further comprising step 1) drying the tissue.

Paragraph 105. The method of Paragraph 104, further comprising step 2) separating collagen from the dried tissue and discarding the collagen.

Paragraph 106. A method of producing an alga tissue extract, comprising the steps of: a) removing a tissue from an alga,
b) breaking up the cells in the tissue,
c) adding a solvent,
d) separating the solvent fraction from a sediment fraction, and.
e) collecting the solvent fraction to obtain the alga tissue extract.

Paragraph 107. The composition of Paragraph 106, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa*, and *Chlorella variabilis*.

Paragraph 108. The composition of Paragraph 106, wherein the tissue is selected from the group consisting of at least one of frond and whole body.

Paragraph 109. The method of Paragraph 106, wherein the solvent is selected from the group consisting of at least one of a polar solvent and a non-polar solvent.

Paragraph 110. The method of Paragraph 106, wherein the polar solvent is selected from the group consisting of at least one of dimethyl sulfoxide (DMSO), isopropyl alcohol, ethanol, methanol, acetic acid and water.

Paragraph 112. The method of Paragraph 106, wherein the non-polar solvent is selected from the group consisting of at least one of hexane, chloroform and ether.

Paragraph 113. The method of Paragraph 106, wherein the method of separating the solvent fraction from the sediment fraction is selected from the group consisting of by gravity, centrifugation, filtration, column chromatography, and HPLC.

Paragraph 114. The method of Paragraph 106, wherein the method of breaking up the cells in the tissue is selected from the group consisting of a blender, homogenizer, grinder, and mortar and pestle.

Paragraph 115. The method of Paragraph 106, further comprising step f) freeze drying the alga tissue extract.

Paragraph 116. The method of Paragraph 106, further comprising step f) lyophilizing the alga tissue extract.

Paragraph 117. The method of Paragraph 106, wherein between step a) and step b) further comprising step 1) freezing the tissue.

Paragraph 118. The method of Paragraph 106, wherein between step a) and step b) further comprising step 1) drying the tissue.

Paragraph 119. A method of producing a bivalve tissue extract, comprising the steps of: a) removing a tissue from a bivalve,
  b) breaking up the cells in the tissue,
  c) adding a solvent,
  d) separating the solvent fraction from a sediment fraction, and
  e) collecting the solvent fraction to obtain the bivalve tissue extract.

Paragraph 120. The composition of Paragraph 119, wherein the bivalve is selected from the group consisting of *Chlamys rubida, Chlamys hastate, Crassotrea gigas, Crassotrea corteziensis*, and *Crassotrea columbiensis*.

Paragraph 121. The composition of Paragraph 119, wherein the tissue is selected from the group consisting of at least one of adductor muscle, viscera, and gonad.

Paragraph 122. The method of Paragraph 119, wherein the solvent is selected from the group consisting of at least one of a polar solvent and a non-polar solvent.

Paragraph 123. The method of Paragraph 119, wherein the polar solvent is selected from the group consisting of at least one of dimethyl sulfoxide (DMSO), isopropyl alcohol, ethanol, methanol, acetic acid and water.

Paragraph 124. The method of Paragraph 119, wherein the non-polar solvent is selected from the group consisting of at least one of hexane, chloroform and ether.

Paragraph 125. The method of Paragraph 119, wherein the method of separating the solvent fraction from the sediment fraction is selected from the group consisting of by gravity, centrifugation, filtration, column chromatography, and HPLC.

Paragraph 126. The method of Paragraph 119, wherein the method of breaking up the cells in the tissue is selected from the group consisting of a blender, homogenizer, grinder, and mortar and pestle.

Paragraph 127. The method of Paragraph 119, further comprising step f) freeze drying the bivalve tissue extract.

Paragraph 128. The method of Paragraph 119, further comprising step f) lyophilizing the bivalve tissue extract.

Paragraph 129. The method of Paragraph 119, wherein between step a) and step b) further comprising step 1) freezing the tissue.

Paragraph 130. The method of Paragraph 119, wherein between step a) and step b) further comprising step 1) drying the tissue.

Paragraph 131. A method of producing a crustacean tissue extract, comprising the steps of:
  a) removing a tissue from a crustacean,
  b) breaking up the cells in the tissue,
  c) adding a solvent,
  d) separating the solvent fraction from a sediment fraction, and
  e) collecting the solvent fraction to obtain the crustacean tissue extract.

Paragraph 132. The composition of Paragraph 131, wherein the crustacean is *Paralothodes camtschaticus*.

Paragraph 133. The composition of Paragraph 131, wherein the tissue is selected from the group consisting of at least one of exoskeleton, muscle, viscera, and gonad.

Paragraph 134. The method of Paragraph 131, wherein the solvent is selected from the group consisting of at least one of a polar solvent and a non-polar solvent.

Paragraph 135. The method of Paragraph 131, wherein the polar solvent is selected from the group consisting of at least one of dimethyl sulfoxide (DMSO), isopropyl alcohol, ethanol, methanol, acetic acid and water.

Paragraph 136. The method of Paragraph 131, wherein the non-polar solvent is selected from the group consisting of at least one of hexane, chloroform and ether.

Paragraph 137. The method of Paragraph 131, wherein the method of separating the solvent fraction from the sediment fraction is selected from the group consisting of by gravity, centrifugation, filtration, column chromatography, and HPLC.

Paragraph 138. The method of Paragraph 131, wherein the method of breaking up the cells in the tissue is selected from the group consisting of a blender, homogenizer, grinder, and mortar and pestle.

Paragraph 139. The method of Paragraph 131, further comprising step f) freeze drying the crustacean tissue extract.

Paragraph 140. The method of Paragraph 131, further comprising step f) lyophilizing the crustacean tissue extract.

Paragraph 141. The method of Paragraph 131, wherein between step a) and step b) further comprising step 1) freezing the tissue.

Paragraph 142. The method of Paragraph 131, wherein between step a) and step b) further comprising step 1) drying the tissue.

Paragraph 143. A method of producing a sea cucumber tissue extract, comprising the steps of:
  a) removing a tissue from a sea cucumber,
  b) breaking up the cells in the tissue,
  c) adding a solvent,
  d) separating the solvent fraction from a sediment fraction, and
  e) collecting the solvent fraction to obtain the sea cucumber tissue extract.

Paragraph 144. The composition of Paragraph 143, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus*, and *Cucumaria japonica*.

Paragraph 145. The composition of Paragraph 143, wherein the tissue is selected from the group consisting of at least one of body wall, muscle, viscera, and gonad.

Paragraph 146. The method of Paragraph 143, wherein the solvent is selected from the group consisting of at least one of a polar solvent and a non-polar solvent.

Paragraph 147. The method of Paragraph 143, wherein the polar solvent is selected from the group consisting of at least one of dimethyl sulfoxide (DMSO), isopropyl alcohol, ethanol, methanol, acetic acid and water.

Paragraph 148. The method of Paragraph 143, wherein the non-polar solvent is selected from the group consisting of at least one of hexane, chloroform and ether.

Paragraph 149. The method of Paragraph 143, wherein the method of separating the solvent fraction from the sediment fraction is selected from the group consisting of by gravity, centrifugation, filtration, column chromatography, and HPLC.

Paragraph 150. The method of Paragraph 143, wherein the method of breaking up the cells in the tissue is selected from the group consisting of a blender, homogenizer, grinder, and mortar and pestle.

Paragraph 151. The method of Paragraph 143, further comprising step f) freeze drying the sea cucumber tissue extract.

Paragraph 152. The method of Paragraph 143, further comprising step f) lyophilizing the sea cucumber tissue extract.

Paragraph 153. The method of Paragraph 143, wherein between step a) and step b) further comprising step 1) freezing the tissue.

Paragraph 154. The method of Paragraph 143, wherein between step a) and step b) further comprising step 1) drying the tissue.

Paragraph 155. A method of producing a cyanobacteria extract, comprising the steps of:
 a) breaking up the cells,
 b) adding a solvent,
 c) separating the solvent fraction from a sediment fraction, and
 d) collecting the solvent fraction to obtain the cyanobacteria extract.

Paragraph 156. The composition of Paragraph 155, wherein the cyanobacteria is selected from the group consisting of *Spirulina pacifica, Arthrospira maxima, Arthrospira planensis, Microcystis aeruginosa*, and *Microcystis wesenbergii*.

Paragraph 157. The method of Paragraph 155, wherein the solvent is selected from the group consisting of at least one of a polar solvent and a non-polar solvent.

Paragraph 158. The method of Paragraph 155, wherein the polar solvent is selected from the group consisting of at least one of dimethyl sulfoxide (DMSO), isopropyl alcohol, ethanol, methanol, acetic acid and water.

Paragraph 159. The method of Paragraph 155, wherein the non-polar solvent is selected from the group consisting of at least one of hexane, chloroform and ether.

Paragraph 160. The method of Paragraph 155, wherein the method of separating the solvent fraction from the sediment fraction is selected from the group consisting of by gravity, centrifugation, filtration, column chromatography, and HPLC.

Paragraph 161. The method of Paragraph 155, wherein the method of breaking up the cells in the tissue is selected from the group consisting of a blender, homogenizer, grinder, and mortar and pestle.

Paragraph 162. The method of Paragraph 155, further comprising step e) freeze drying the cyanobacteria extract.

Paragraph 163. The method of Paragraph 155, further comprising step e) lyophilizing the cyanobacteria extract.

Paragraph 164. The method of Paragraph 155, wherein before step a) further comprising step 1) freezing the cyanobacteria.

Paragraph 165. The method of Paragraph 155, wherein before step a) further comprising step 1) drying the cyanobacteria.

Paragraph 166. A method of treating skin, comprising the steps of:
 a) topically applying a composition comprising an abalone tissue extract to the surface of the skin with a skin ailment, and
 b) applying the composition for at least 7 days.

Paragraph 167. The method of Paragraph 166, wherein the skin ailment is selected from the group consisting of fine lines, wrinkles, sagging, large pores, lentigines, keratoses, rosacea, dry skin, irritated skin and sensitive skin.

Paragraph 168. The method of Paragraph 166, wherein the skin ailment is due to a cause selected from the group consisting of sun light, ultraviolet light, wind, heat, humidity, soaps, age and health.

Paragraph 169. A method of treating skin, comprising the steps of:
 a) topically applying a composition comprising an alga tissue extract to the surface of the skin with a skin ailment, and
 b) applying the composition for at least 7 days.

Paragraph 170. The method of Paragraph 169, wherein the skin ailment is selected from the group consisting of fine lines, wrinkles, sagging, large pores, lentigines, keratoses, rosacea, dry skin, irritated skin and sensitive skin.

Paragraph 171. The method of Paragraph 169, wherein the skin ailment is due to a cause selected from the group consisting of sun light, ultraviolet light, wind, heat, humidity, soaps, age and health.

Paragraph 172. A method of treating skin, comprising the steps of:
 a) topically applying a composition comprising a bivalve tissue extract to the surface of the skin with a skin ailment, and
 b) applying the composition for at least 7 days.

Paragraph 173. The method of Paragraph 172, wherein the skin ailment is selected from the group consisting of fine lines, wrinkles, sagging, large pores, lentigines, keratoses, rosacea, dry skin, irritated skin and sensitive skin.

Paragraph 174. The method of Paragraph 172, wherein the skin ailment is due to a cause selected from the group consisting of sun light, ultraviolet light, wind, heat, humidity, soaps, age and health.

Paragraph 175. A method of treating skin, comprising the steps of:
 a) topically applying a composition comprising a crustacean tissue extract to the surface of the skin with a skin ailment, and
 b) applying the composition for at least 7 days.

Paragraph 176. The method of Paragraph 175, wherein the skin ailment is selected from the group consisting of fine lines, wrinkles, sagging, large pores, lentigines, keratoses, rosacea, dry skin, irritated skin and sensitive skin.

Paragraph 177. The method of Paragraph 175, wherein the skin ailment is due to a cause selected from the group consisting of sun light, ultraviolet light, wind, heat, humidity, soaps, age and health.

Paragraph 178. A method of treating skin, comprising the steps of:
 a) topically applying a composition comprising a sea cucumber tissue extract to the surface of the skin with a skin ailment, and
 b) applying the composition for at least 7 days.

Paragraph 179. The method of Paragraph 178, wherein the skin ailment is selected from the group consisting of fine lines, wrinkles, sagging, large pores, lentigines, keratoses, rosacea, dry skin, irritated skin and sensitive skin.

Paragraph 180. The method of Paragraph 178, wherein the skin ailment is due to a cause selected from the group consisting of sun light, ultraviolet light, wind, heat, humidity, soaps, age and health.

Paragraph 181. A method of treating skin, comprising the steps of:
a) topically applying a composition comprising a cyanobacteria extract to the surface of the skin with a skin ailment, and
b) applying the composition for at least 7 days.

Paragraph 182. The method of Paragraph 181, wherein the skin ailment is selected from the group consisting of fine lines, wrinkles, sagging, large pores, lentigines, keratoses, rosacea, dry skin, irritated skin and sensitive skin.

Paragraph 183. The method of Paragraph 181, wherein the skin ailment is due to a cause selected from the group consisting of sun light, ultraviolet light, wind, heat, humidity, soaps, age and health.

Paragraph 184. A method of increasing the production of Hyaluronic acid, comprising the steps of:
a) topically applying a composition comprising an abalone tissue extract to the surface of the skin with a skin ailment, and
b) applying the composition for at least 7 days.

Paragraph 185. A method of increasing the production of elastin, comprising the steps of:
a) topically applying a composition comprising an abalone tissue extract to the surface of the skin with a skin ailment, and
b) applying the composition for at least 7 days.

Paragraph 186. A method of increasing the production of collagen, comprising the steps of:
a) topically applying a composition comprising an abalone tissue extract to the surface of the skin with a skin ailment, and
b) applying the composition for at least 7 days.

Paragraph 187. A method of increasing the production of Hyaluronic acid, comprising the steps of:
a) topically applying a composition comprising an alga tissue extract to the surface of the skin with a skin ailment, and
b) applying the composition for at least 7 days.

Paragraph 188. A method of increasing the production of elastin, comprising the steps of:
a) topically applying a composition comprising an alga tissue extract to the surface of the skin with a skin ailment, and
b) applying the composition for at least 7 days.

Paragraph 189. A method of increasing the production of collagen, comprising the steps of:
a) topically applying a composition comprising an alga tissue extract to the surface of the skin with a skin ailment, and
b) applying the composition for at least 7 days.

Paragraph 190. A method of increasing the production of Hyaluronic acid, comprising the steps of:
a) topically applying a composition comprising a bivalve tissue extract to the surface of the skin with a skin ailment, and
b) applying the composition for at least 7 days.

Paragraph 191. A method of increasing the production of elastin, comprising the steps of:
a) topically applying a composition comprising a bivalve tissue extract to the surface of the skin with a skin ailment, and
b) applying the composition for at least 7 days.

Paragraph 192. A method of increasing the production of collagen, comprising the steps of:
a) topically applying a composition comprising a bivalve tissue extract to the surface of the skin with a skin ailment, and
b) applying the composition for at least 7 days.

Paragraph 193. A method of increasing the production of Hyaluronic acid, comprising the steps of:
a) topically applying a composition comprising a crustacean tissue extract to the surface of the skin with a skin ailment, and
b) applying the composition for at least 7 days.

Paragraph 194. A method of increasing the production of elastin, comprising the steps of:
a) topically applying a composition comprising a crustacean tissue extract to the surface of the skin with a skin ailment, and
b) applying the composition for at least 7 days.

Paragraph 195. A method of increasing the production of collagen, comprising the steps of:
a) topically applying a composition comprising a crustacean tissue extract to the surface of the skin with a skin ailment, and
b) applying the composition for at least 7 days.

Paragraph 196. A method of increasing the production of Hyaluronic acid, comprising the steps of:
a) topically applying a composition comprising a sea cucumber tissue extract to the surface of the skin with a skin ailment, and
b) applying the composition for at least 7 days.

Paragraph 197. A method of increasing the production of elastin, comprising the steps of:
a) topically applying a composition comprising a sea cucumber tissue extract to the surface of the skin with a skin ailment, and
b) applying the composition for at least 7 days.

Paragraph 198. A method of increasing the production of collagen, comprising the steps of:
a) topically applying a composition comprising a sea cucumber tissue extract to the surface of the skin with a skin ailment, and
b) applying the composition for at least 7 days.

Paragraph 199. A method of increasing the production of Hyaluronic acid, comprising the steps of:
a) topically applying a composition comprising a cyanobacteria extract to the surface of the skin with a skin ailment, and
b) applying the composition for at least 7 days.

Paragraph 200. A method of increasing the production of elastin, comprising the steps of:
a) topically applying a composition comprising a cyanobacteria extract to the surface of the skin with a skin ailment, and
b) applying the composition for at least 7 days.

Paragraph 201. A method of increasing the production of collagen, comprising the steps of:
a) topically applying a composition comprising a cyanobacteria extract to the surface of the skin with a skin ailment, and
b) applying the composition for at least 7 days.

Paragraph 202. A product of the process, comprising the steps of:
a) removing a tissue from an abalone,
b) breaking up the cells in the tissue,
c) adding a solvent, d) separating the solvent fraction from a sediment fraction, and.

e) collecting the solvent fraction to obtain the abalone tissue extract.

Paragraph 203. The product of the process of Paragraph 202, wherein the abalone is *Haliotis* spp.

Paragraph 204. The product of the process of Paragraph 203, wherein the *Haliotis* spp. is selected from the group consisting of *Haliotis fulgens, Haliotis rufescens, Haliotis corrugata, Haliotis kamtschatkana*, and *Haliotis walallensis*.

Paragraph 205. The product of the process of Paragraph 202, wherein the abalone is a hybrid abalone.

Paragraph 206. The product of the process of Paragraph 205, wherein the hybrid abalone is selected from the group consisting of *Haliotis rufescens×Haliotis* corrugate, *Haliotis rufescens×Haliotis fulgens*, and *Haliotis rufescens×Haliotis laevagata*.

Paragraph 207. The product of the process of Paragraph 202, wherein the tissue is selected from the group consisting of at least one of muscle, viscera, conical appendage, digestive gland, gonad, testes and ovary.

Paragraph 208. The product of the process of Paragraph 202, wherein the solvent is selected from the group consisting of at least one of a polar solvent and a non-polar solvent.

Paragraph 209. The product of the process of Paragraph 202, wherein the polar solvent is selected from the group consisting of at least one of dimethyl sulfoxide (DMSO), isopropyl alcohol, ethanol, methanol, acetic acid and water.

Paragraph 210. The product of the process of Paragraph 202, wherein the non-polar solvent is selected from the group consisting of at least one of hexane, chloroform and ether.

Paragraph 211. The product of the process of Paragraph 202, wherein The product of the process of separating the solvent fraction from the sediment fraction is selected from the group consisting of by gravity, centrifugation, filtration, column chromatography, and HPLC.

Paragraph 212. The product of the process of Paragraph 202, wherein The product of the process of breaking up the cells in the tissue is selected from the group consisting of a blender, homogenizer, grinder, and mortar and pestle.

Paragraph 213. The product of the process of Paragraph 202, further comprising step f) freeze drying the abalone tissue extract.

Paragraph 214. The product of the process of Paragraph 202, further comprising step f) lyophilizing the abalone tissue extract.

Paragraph 215. The product of the process of Paragraph 202, wherein between step a) and step b) further comprising step 1) freezing the tissue.

Paragraph 216. The product of the process of Paragraph 202, wherein between step a) and step b) further comprising step 1) drying the tissue.

Paragraph 217. The product of the process of Paragraph 104, further comprising step 2) separating collagen from the dried tissue and discarding the collagen.

Paragraph 218. A product of the process, comprising the steps of:

a) removing a tissue from an alga, b) breaking up the cells in the tissue, c) adding a solvent, d) separating the solvent fraction from a sediment fraction, and.

e) collecting the solvent fraction to obtain the alga tissue extract.

Paragraph 219. The composition of Paragraph 218, wherein the alga is selected from the group consisting of *Macrocystis integrifolia, Macrocystis pyrifera, Fucus vesiculosis, Ascophyllum nodosum, Spirulina pacifica, Sargassum muticum, Chlorella pyrenoidosa*, and *Chlorella variabilis*.

Paragraph 220. The composition of Paragraph 218, wherein the tissue is selected from the group consisting of at least one of frond and whole body.

Paragraph 221. The product of the process of Paragraph 218, wherein the solvent is selected from the group consisting of at least one of a polar solvent and a non-polar solvent.

Paragraph 222. The product of the process of Paragraph 218, wherein the polar solvent is selected from the group consisting of at least one of dimethyl sulfoxide (DMSO), isopropyl alcohol, ethanol, methanol, acetic acid and water.

Paragraph 223. The product of the process of Paragraph 218, wherein the non-polar solvent is selected from the group consisting of at least one of hexane, chloroform and ether.

Paragraph 224. The product of the process of Paragraph 218, wherein The product of the process of separating the solvent fraction from the sediment fraction is selected from the group consisting of by gravity, centrifugation, filtration, column chromatography, and HPLC.

Paragraph 225. The product of the process of Paragraph 218, wherein The product of the process of breaking up the cells in the tissue is selected from the group consisting of a blender, homogenizer, grinder, and mortar and pestle.

Paragraph 226. The product of the process of Paragraph 218, further comprising step f) freeze drying the alga tissue extract.

Paragraph 227. The product of the process of Paragraph 218, further comprising step f) lyophilizing the alga tissue extract.

Paragraph 228. The product of the process of Paragraph 218, wherein between step a) and step b) further comprising step 1) freezing the tissue.

Paragraph 229. The product of the process of Paragraph 218, wherein between step a) and step b) further comprising step 1) drying the tissue.

Paragraph 230. A product of the process, comprising the steps of:

a) removing a tissue from a bivalve, b) breaking up the cells in the tissue, c) adding a solvent, d) separating the solvent fraction from a sediment fraction, and e) collecting the solvent fraction to obtain the bivalve tissue extract.

Paragraph 231. The composition of Paragraph 230, wherein the bivalve is selected from the group consisting of *Chlamys rubida, Chlamys hastate, Crassotrea gigas, Crassotrea corteziensis*, and *Crassotrea columbiensis*.

Paragraph 232. The composition of Paragraph 230, wherein the tissue is selected from the group consisting of at least one of adductor muscle, viscera, and gonad.

Paragraph 233. The product of the process of Paragraph 230, wherein the solvent is selected from the group consisting of at least one of a polar solvent and a non-polar solvent.

Paragraph 234. The product of the process of Paragraph 230, wherein the polar solvent is selected from the group consisting of at least one of dimethyl sulfoxide (DMSO), isopropyl alcohol, ethanol, methanol, acetic acid and water.

Paragraph 235. The product of the process of Paragraph 230, wherein the non-polar solvent is selected from the group consisting of at least one of hexane, chloroform and ether.

Paragraph 236. The product of the process of Paragraph 230, wherein The product of the process of separating the solvent fraction from the sediment fraction is selected from the group consisting of by gravity, centrifugation, filtration, column chromatography, and HPLC.

Paragraph 237. The product of the process of Paragraph 230, wherein The product of the process of breaking up the cells in the tissue is selected from the group consisting of a blender, homogenizer, grinder, and mortar and pestle.

Paragraph 238. The product of the process of Paragraph 230, further comprising step f) freeze drying the bivalve tissue extract.

Paragraph 239. The product of the process of Paragraph 230, further comprising step f) lyophilizing the bivalve tissue extract.

Paragraph 240. The product of the process of Paragraph 230, wherein between step a) and step b) further comprising step 1) freezing the tissue.

Paragraph 241. The product of the process of Paragraph 230, wherein between step a) and step b) further comprising step 1) drying the tissue.

Paragraph 242. A product of the process, comprising the steps of:
 a) removing a tissue from a crustacean,
 b) breaking up the cells in the tissue,
 c) adding a solvent,
 d) separating the solvent fraction from a sediment fraction, and
 e) collecting the solvent fraction to obtain the crustacean tissue extract.

Paragraph 243. The composition of Paragraph 242, wherein the crustacean is *Paralothodes camtschaticus*.

Paragraph 244. The composition of Paragraph 242, wherein the tissue is selected from the group consisting of at least one of exoskeleton, muscle, viscera, and gonad.

Paragraph 245. The product of the process of Paragraph 242, wherein the solvent is selected from the group consisting of at least one of a polar solvent and a non-polar solvent.

Paragraph 246. The product of the process of Paragraph 242, wherein the polar solvent is selected from the group consisting of at least one of dimethyl sulfoxide (DMSO), isopropyl alcohol, ethanol, methanol, acetic acid and water.

Paragraph 247. The product of the process of Paragraph 242, wherein the non-polar solvent is selected from the group consisting of at least one of hexane, chloroform and ether.

Paragraph 248. The product of the process of Paragraph 242, wherein The product of the process of separating the solvent fraction from the sediment fraction is selected from the group consisting of by gravity, centrifugation, filtration, column chromatography, and HPLC.

Paragraph 249. The product of the process of Paragraph 242, wherein The product of the process of breaking up the cells in the tissue is selected from the group consisting of a blender, homogenizer, grinder, and mortar and pestle.

Paragraph 250. The product of the process of Paragraph 242, further comprising step f) freeze drying the crustacean tissue extract.

Paragraph 251. The product of the process of Paragraph 242, further comprising step f) lyophilizing the crustacean tissue extract.

Paragraph 252. The product of the process of Paragraph 242, wherein between step a) and step b) further comprising step 1) freezing the tissue.

Paragraph 253. The product of the process of Paragraph 242, wherein between step a) and step b) further comprising step 1) drying the tissue.

Paragraph 254. A product of the process, comprising the steps of:
 a) removing a tissue from a sea cucumber,
 b) breaking up the cells in the tissue,
 c) adding a solvent,
 d) separating the solvent fraction from a sediment fraction, and
 e) collecting the solvent fraction to obtain the sea cucumber tissue extract.

Paragraph 255. The composition of Paragraph 254, wherein the sea cucumber is selected from the group consisting of *Holothuria mexicana, Holothuria californicus, Holothuria scabra, Stichopus chlorontus, Stichopus horrens, Stichopus japonicus, Apostichopus japonicus*, and *Cucumaria japonica*.

Paragraph 256. The composition of Paragraph 254, wherein the tissue is selected from the group consisting of at least one of body wall, muscle, viscera, and gonad.

Paragraph 257. The product of the process of Paragraph 254, wherein the solvent is selected from the group consisting of at least one of a polar solvent and a non-polar solvent.

Paragraph 258. The product of the process of Paragraph 254, wherein the polar solvent is selected from the group consisting of at least one of dimethyl sulfoxide (DMSO), isopropyl alcohol, ethanol, methanol, acetic acid and water.

Paragraph 259. The product of the process of Paragraph 254, wherein the non-polar solvent is selected from the group consisting of at least one of hexane, chloroform and ether.

Paragraph 260. The product of the process of Paragraph 254, wherein The product of the process of separating the solvent fraction from the sediment fraction is selected from the group consisting of by gravity, centrifugation, filtration, column chromatography, and HPLC.

Paragraph 261. The product of the process of Paragraph 254, wherein The product of the process of breaking up the cells in the tissue is selected from the group consisting of a blender, homogenizer, grinder, and mortar and pestle.

Paragraph 262. The product of the process of Paragraph 254, further comprising step f) freeze drying the sea cucumber tissue extract.

Paragraph 263. The product of the process of Paragraph 254, further comprising step f) lyophilizing the sea cucumber tissue extract.

Paragraph 264. The product of the process of Paragraph 254, wherein between step a) and step b) further comprising step 1) freezing the tissue.

Paragraph 265. The product of the process of Paragraph 254, wherein between step a) and step b) further comprising step 1) drying the tissue.

Paragraph 266. A product of the process, comprising the steps of:
 a) breaking up the cells,
 b) adding a solvent,
 c) separating the solvent fraction from a sediment fraction, and
 d) collecting the solvent fraction to obtain the cyanobacteria extract.

Paragraph 267. The composition of Paragraph 266, wherein the cyanobacteria is selected from the group consisting of *Spirulina pacifica, Arthrospira maxima, Arthrospira planensis, Microcystis aeruginosa,* and *Microcystis wesenbergii.*

Paragraph 268. The product of the process of Paragraph 266, wherein the solvent is selected from the group consisting of at least one of a polar solvent and a non-polar solvent.

Paragraph 269. The product of the process of Paragraph 266, wherein the polar solvent is selected from the group consisting of at least one of dimethyl sulfoxide (DMSO), isopropyl alcohol, ethanol, methanol, acetic acid and water.

Paragraph 270. The product of the process of Paragraph 266, wherein the non-polar solvent is selected from the group consisting of at least one of hexane, chloroform and ether.

Paragraph 271. The product of the process of Paragraph 266, wherein The product of the process of separating the solvent fraction from the sediment fraction is selected from the group consisting of by gravity, centrifugation, filtration, column chromatography, and HPLC.

Paragraph 272. The product of the process of Paragraph 266, wherein The product of the process of breaking up the cells in the tissue is selected from the group consisting of a blender, homogenizer, grinder, and mortar and pestle.

Paragraph 273. The product of the process of Paragraph 266, further comprising step e) freeze drying the cyanobacteria extract.

Paragraph 274. The product of the process of Paragraph 266, further comprising step e) lyophilizing the cyanobacteria extract.

Paragraph 275. The product of the process of Paragraph 266, wherein before step a) further comprising step 1) freezing the cyanobacteria.

Paragraph 276. The product of the process of Paragraph 266, wherein before step a) further comprising step 1) drying the cyanobacteria.

Paragraph 277. A method of Paragraph 166, wherein the applying the composition is for at least 14 days.

Paragraph 278. A method of Paragraph 277, wherein the applying the composition is for at least 30 days.

Paragraph 279. A method of Paragraph 169, wherein the applying the composition is for at least 14 days.

Paragraph 280. A method of Paragraph 279, wherein the applying the composition is for at least 30 days.

Paragraph 281. A method of Paragraph 172, wherein the applying the composition is for at least 14 days.

Paragraph 282. A method of Paragraph 281, wherein the applying the composition is for at least 30 days.

Paragraph 283. A method of Paragraph 175, wherein the applying the composition is for at least 14 days.

Paragraph 284. A method of Paragraph 283, wherein the applying the composition is for at least 30 days.

Paragraph 285. A method of Paragraph 178, wherein the applying the composition is for at least 14 days.

Paragraph 286. A method of Paragraph 285, wherein the applying the composition is for at least 30 days.

Paragraph 287. A method of Paragraph 181, wherein the applying the composition is for at least 14 days.

Paragraph 288. A method of Paragraph 287, wherein the applying the composition is for at least 30 days.

Beneficial Effects of Extracts

Regeneration of the skin to reestablish permanent improvement and "skin age" of decades earlier.

Healing of the ulcers of the skin of the elderly and diabetics.

Used for diabetic skin to regenerate the blood vessels that have been destroyed or altered by diabetes.

Improve the thickness and function of all skin that it is applied to, and most specifically bruising and extreme weakness of skin of the elderly. This product not only minimizes the bruising but adds strength to minimize any tearing of the skin.

Increasing the thickness, strength and elasticity of the skin, wrinkles of all sorts, especially of sun damaged or aged skin (vs. muscular wrinkles) can be virtually erased. And even muscular wrinkles e.g. between the eyes and in the laugh lines can be minimized with this product.

Stimulation of the immune system is through the T cell mediated system, which is the most efficient way of killing pre-cancers and cancers.

Systemic absorption of this product will also be used as a supplement to strengthen the internal organs similar to the effects of the skin in topical application.

Systemic administration will be used to treat internal carcinomas and sarcomas.

Effective against rosacea and other prominent cutaneous blood vessel abnormalities.

Can be used in cream, gel, plasma, lotion, ointment, powder, capsule, tablet, liquid, spray, foam, solution, facial mask, skin mask, topical application, etc.

EXAMPLES

Extract Trial Study

Figure 2:
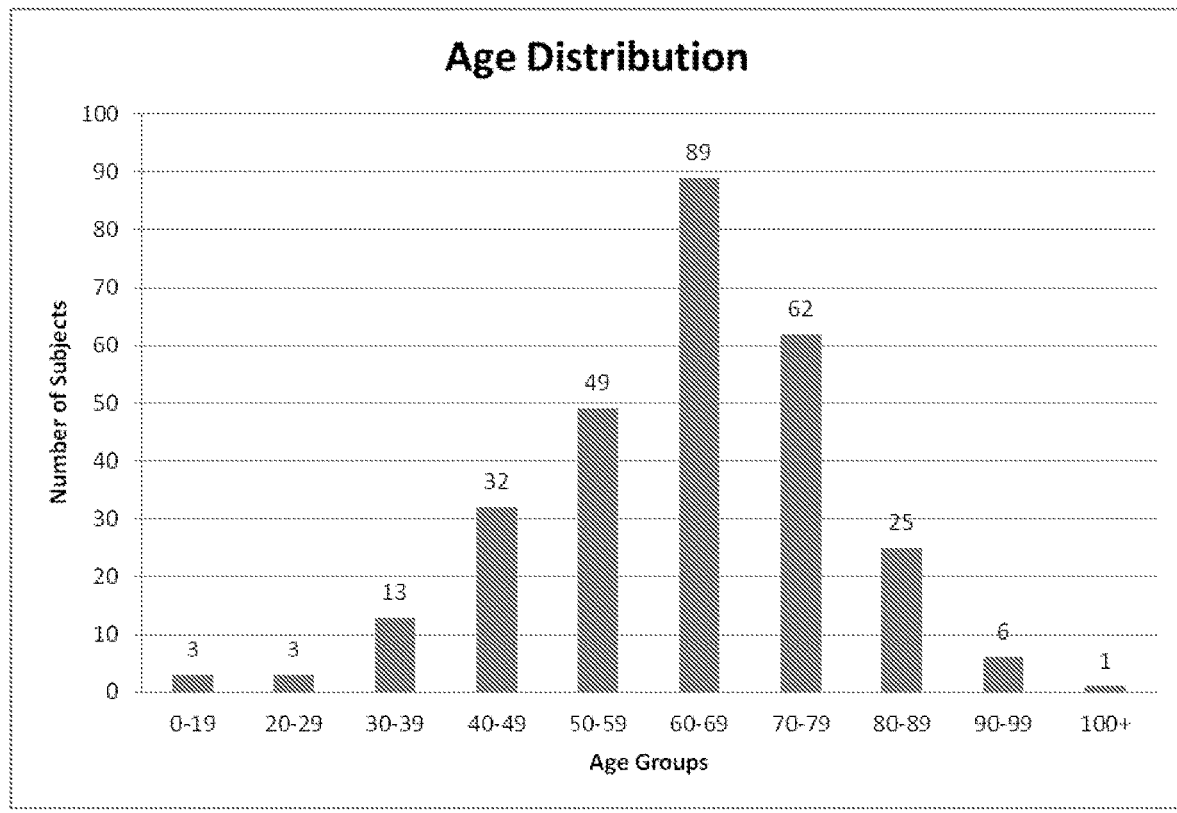
FIG. 2 shows the age distribution of the patients in the study of the extract composition.

The study had a sample size of 283 people and none of the subjects dropped out during the study. The distribution of subjects was 151 males and 132 females (FIG. 1), and an age distribution from 14 to 101 years (FIG. 2). The ethnicity of the subjects was 275 Caucasians, 6 Asians and 2 African-American.

Table 1 shows the distribution of skin of afflictions with age distribution.

TABLE 1

| Age Groups | Number and (%) of subjects in each group | Number and (%) of subjects with Wrinkles | Number and (%) of subjects with "Rosacea" | Number and (%) of subjects with Bruising | Number and (%) of subjects with Thin Skin |
|---|---|---|---|---|---|
| 0-19 | 3 (1.06%) | 0 (0%) | 0 (0%) | 0 (0%) | 0 (0%) |
| 20-29 | 3 (1.06%) | 0 (0%) | 1 (33.3%) | 0 (0%) | 0 (0%) |
| 30-39 | 13 (4.59%) | 5 (38.5%) | 3 (23.1%) | 0 (0%) | 1 (7.7%) |
| 40-49 | 32 (11.30%) | 28 (87.50%) | 5 (15.6%) | 2 (6.3%) | 18 (56.3%) |
| 50-59 | 49 (17.31%) | 49 (100%) | 9 (18.4%) | 11 (22.4%) | 40 (81.6%) |

TABLE 1-continued

| Age Groups | Number and (%) of subjects in each group | Number and (%) of subjects with Wrinkles | Number and (%) of subjects with "Rosacea" | Number and (%) of subjects with Bruising | Number and (%) of subjects with Thin Skin |
|---|---|---|---|---|---|
| 60-69 | 89 (31.44%) | 89 (100%) | 35 (39.3%) | 67 (75.3%) | 89 (100%) |
| 70-79 | 62 (21.90%) | 62 (100%) | 41 (66.1%) | 57 (92%) | 62 (100%) |
| 80-89 | 25 (8.83%) | 25 (100%) | 20 (80%) | 25 (100%) | 25 (100%) |
| 90-99 | 6 (2.12%) | 6 (100%) | 6 (100%) | 6 (100%) | 6 (100%) |
| 100+ | 1 (0.35%) | 1 (100%) | 1 (100%) | 1 (100%) | 1 (100%) |

None of the subjects had an allergic reactions, even though 14 subjects had seafood allergies. Five to 15 treatments of the extract composition led to substantial improvement. 95% of subjects saw across the board improvements after 15 applications: lessening of wrinkles, thickening of the skin.

Figure 3:
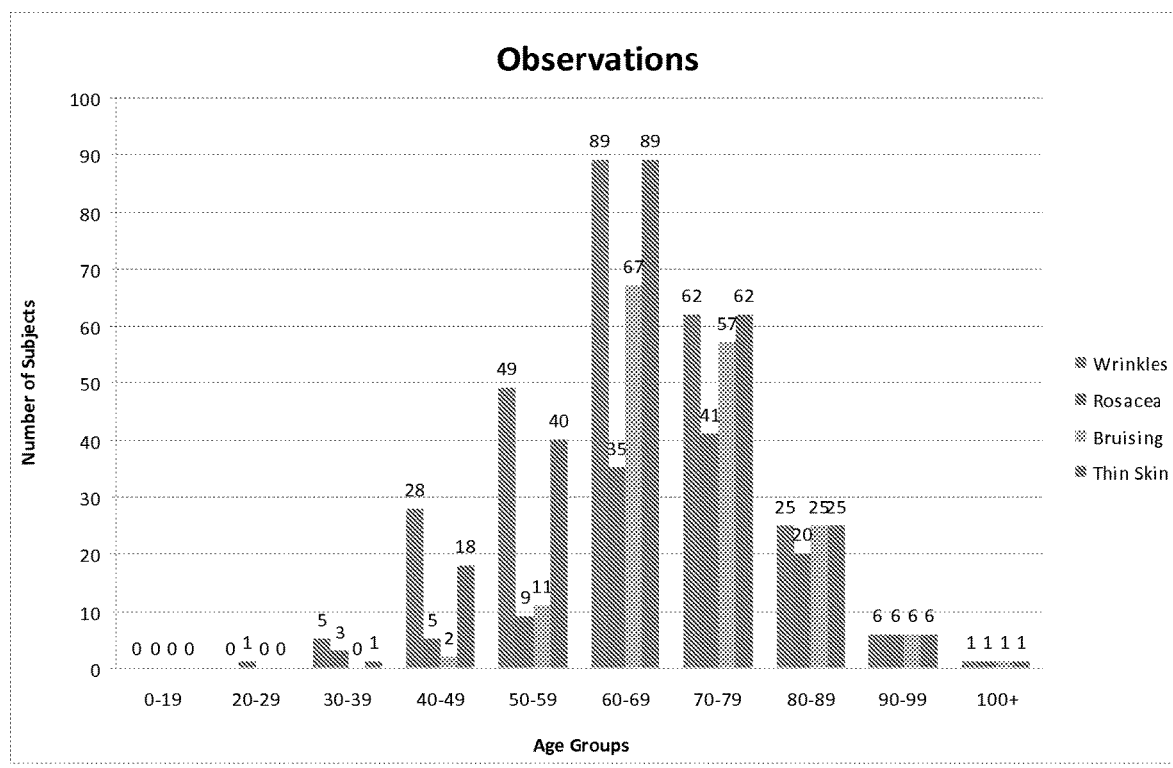
FIG. 3 shows the percentage of patients in each age group who showed improvement in wrinkles, rosacea, bruising and thin skin after the use of the extract composition.

The first observed improvement was the fine wrinkles over the face (FIG. 3). Four to 5 treatments were enough for 60% of the subjects to notice improvements in the cheek wrinkles. Similar improvements on the lower eyelids are expected after 5 to 15 treatments. The first areas of improvement are under the eyelids followed by wrinkles, thin skin, and the disappearance of rosacea. Rosacea improved or disappeared after 20-30 treatments.

The last observed effect was the disappearance of bruising of the skin. Approximately, 60-75% of the subjects had noticeable differences by $30^{th}$ application. The improvement is exponential after about the $15^{th}$ application.

50% of the subjects had 50% improvement in fine wrinkles of the face after 15 applications and 100% of the subjects had 50% or more improvement after 30 applications 20% of the subjects saw a significant improvement in thin skin after 15 applications 95% of subjects in 30 applications 10% of subjects saw significant changes in Rosacea after 15 applications and 95% of subjects saw significant changes after 30 applications 0% of the subjects saw significant changes in bruising after 15 applications and 65% of the subjects saw significant changes from 30 applications Histological Examination of Pre-Treatment and Post-Treatment Biopsies A 60 year old male applied the extract to the surface on the top of one hand for 30 days. The other hand remained un-treated. After the completion of the 30 days of treatment, a 2 mm biopsies of skin were taken from both the treated and untreated hand.

The skin biopsies were prepared for histological examination and stained with hematoxyln and eosin.

Figure 4:
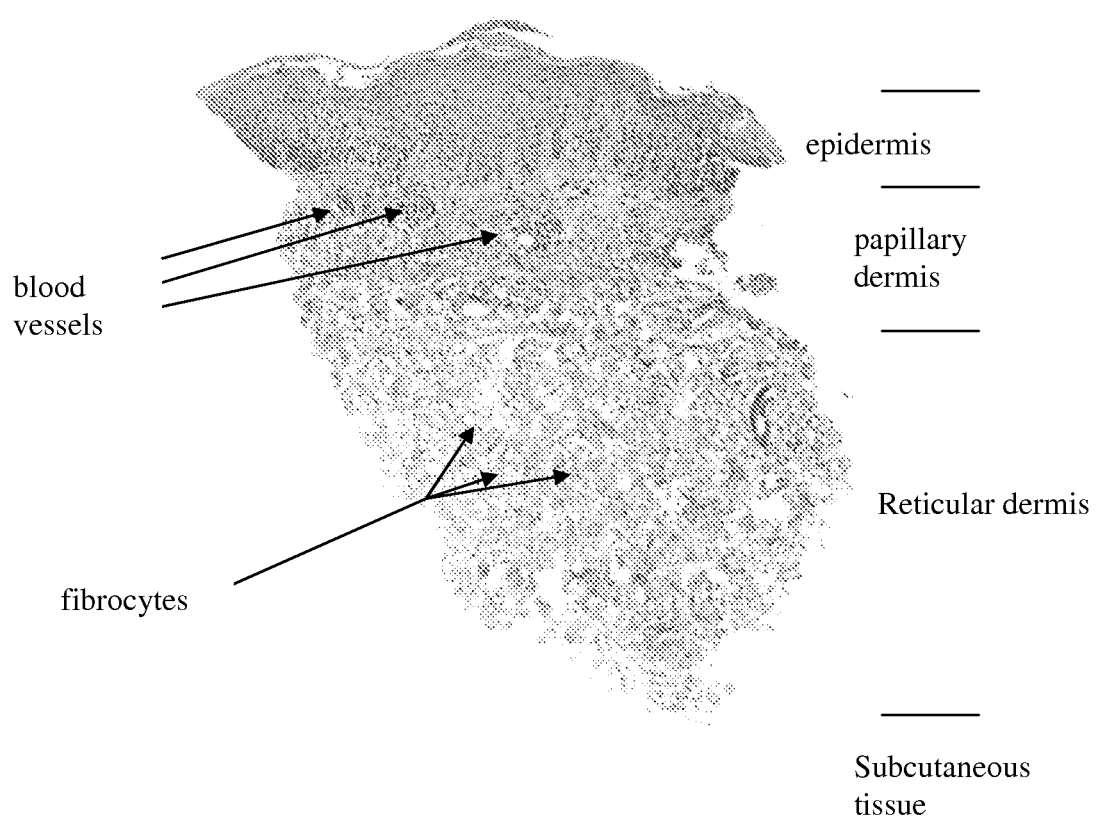
FIG. 4 is a photograph showing the histology of a tissue sample from the hand of a patient after treatment with the extract composition.
Figure 5:
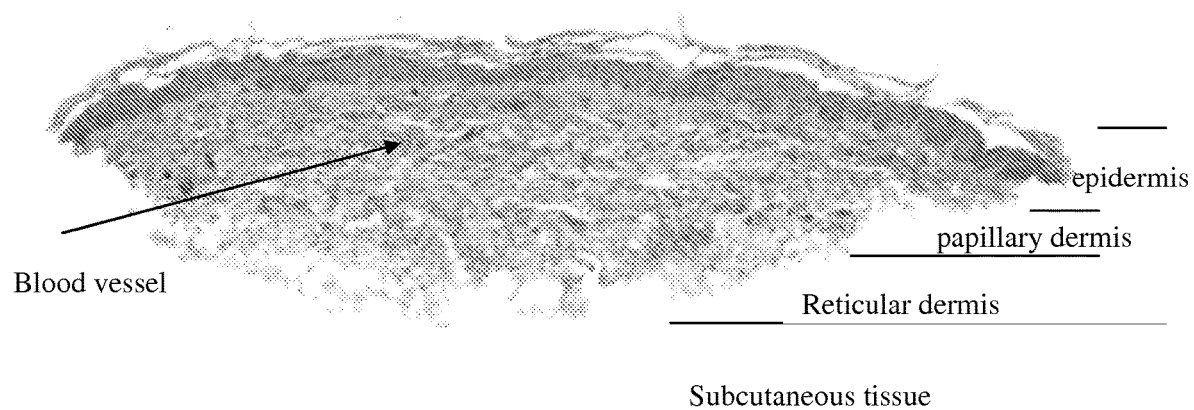
FIG. 5 is a photograph showing the histology of a tissue sample from the hand of a patient before treatment with the extract composition.

A microscopic examination of the biopsies showed that there were 35 times more fibrocytes (producers of collagen, elastin and hyaluronic acid) in the post-treatment sample (FIG. 4) compared to the pre-treatment sample (FIG. 5).

The pre-treatment sample had only one blood vessel in the biopsies compared to thirteen blood vessels in the post-treatment, even though it was the same amount of tissue. The increase in the number of blood vessels facilitates the distributions of the raw materials needed for improving the skin.

The epidermis in pre-treatment tissue biopsy is thin with degenerative collagen, which is characteristic of sun-damaged and aged skin compared to the epidermis in post-treatment tissue biopsies which is thicker with healthy collagen. The post-treatment tissue sample has many young cells that are huge, plump and vivacious.

The post-treatment biopsy contracted almost 33% in length and width due to regained elasticity. The post-treatment is actually 33% wider and 33 thicker than shown compared to the pre-treatment biopsy. (Tissue samples shown at 40× magnification).

Figure 6:
FIG. 6 is a photograph of the hands of a patient showing the physical appearance before treatment (right hand) and after treatment (left hand) with the extract composition.

A visual examination of the skin on the hands showed a noticeable difference in appearance between the treated and untreated hands (FIG. 6)

Effects of Extracts

The extracts from the disclosed marine organisms (abalone, algae, cyanobacteria, bivalves, sea cucumbers and crustaceans have been found to rejuvenate the epidermis and papillary dermis, stimulate the production of fibrocytes and capillaries; stimulate the fibrocytes to produce collagen, elastin and hyaluronic acid; stimulate Langerhan's cells to activate T cells to kill malignant cells, stimulate development of granulation tissue and reepithelialization of wounds, ulcers and burns. Additionally, the extracts contain antioxidants, polypeptides, vitamins, minerals, and antifungal and antibacterial agents that assist the active ingredients in producing the observed effects.

The invention claimed is:

1. A topical composition comprising a first tissue extract from abalone and a second tissue extract from a sea cucumber, wherein, wherein the topical composition is suitable for dermatologic application, wherein the topical composition is a gel, cream, plasma, lotion, foam, facial mask, or skin mask, wherein the first tissue extract and the second tissue extract are present at concentrations such that composition is therapeutically effective to treat a subject affected with rosacea, and wherein the second tissue extract is produced by a process of extraction by a polar solvent.

2. The composition of claim 1 wherein when applied daily to skin for 30 days to a subject in need results in a significant improvement of one or more of fine wrinkles, easily bruised skin, and thin skin.

3. The composition of claim 1 wherein the polar solvent is selected from the group consisting of dimethyl sulfoxide (DMSO), isopropyl alcohol, ethanol, methanol, and acetic acid.

4. The composition of claim 3 wherein the polar solvent is DMSO.

5. The composition of claim 1 wherein the abalone tissue extract is a polar solvent extract, a non-polar solvent extract, or a combination thereof.

6. The composition of claim 1 wherein the sea cucumber is selected from the group consisting of *Holothuria mexicana, Holothuria californica, Holothuria scabra, Stichopus chlorontus, Stichopus horrens, Stichopus japonicus, Apostichopus japonicus*, and *Cucumaria japonica*.

7. The composition of claim 1 wherein the second tissue extract is extracted from at least one sea cucumber part selected from the group consisting of body walls, muscles, visceras, and gonads.

8. The composition of claim 1 wherein the second tissue extract is produced by a process of extraction by a dimethyl sulfoxide, wherein the topical composition is suitable for dermatologic application and wherein application of the composition to the skin of a subject causes an increase in production of collagen, elastin, hyaluronic acid, fibrocytes, and new blood vessels.

9. A method of treatment of a subject in need thereof comprising the step of topically administering a composition of claim 1 wherein the subject in need thereof has a skin ailment.

10. The method of claim 9 wherein the skin ailment is selected from the group consisting of fine lines, wrinkles, sagging, large pores, lentigines, keratosis, rosacea, dry skin, irritated skin and sensitive skin.

11. The method of claim 10 wherein the skin ailment is due to a cause selected from the group consisting of sun light, ultraviolet light, wind, heat, humidity, soaps, age and health.

12. The composition of claim 1 further comprising at least a third tissue extract selected from algae, bivalves, crustaceans, or cyanobacteria.

* * * * *